(12) United States Patent
Ataee et al.

(10) Patent No.: US 9,389,694 B2
(45) Date of Patent: Jul. 12, 2016

(54) SYSTEMS, ARTICLES, AND METHODS FOR GESTURE IDENTIFICATION IN WEARABLE ELECTROMYOGRAPHY DEVICES

(71) Applicant: Thalmic Labs Inc., Kitchener (CA)

(72) Inventors: Pedram Ataee, Waterloo (CA); Idris S. Aleem, Pickering (CA); Matthew Bailey, Kitchener (CA)

(73) Assignee: THALMIC LABS INC., Kitchener (CA)

(*) Notice: Subject to any disclaimer, the term of this patent is extended or adjusted under 35 U.S.C. 154(b) by 57 days.

(21) Appl. No.: 14/520,081

(22) Filed: Oct. 21, 2014

(65) Prior Publication Data

US 2015/0109202 A1   Apr. 23, 2015

Related U.S. Application Data

(60) Provisional application No. 61/894,263, filed on Oct. 22, 2013.

(51) Int. Cl.
*G06F 3/01* (2006.01)
*A61B 5/00* (2006.01)
*A61B 5/0488* (2006.01)

(52) U.S. Cl.
CPC .............. *G06F 3/017* (2013.01); *A61B 5/0488* (2013.01); *A61B 5/681* (2013.01); *A61B 5/7267* (2013.01); *A61B 2562/063* (2013.01)

(58) Field of Classification Search
CPC ... G06F 19/3406; G06F 19/3475; G06F 3/01; G06F 3/012; G06F 3/013; G06F 3/015; G06F 3/038; G06F 3/0484; G06F 9/4843
See application file for complete search history.

(56) References Cited

U.S. PATENT DOCUMENTS

2009/0326406 A1* 12/2009 Tan .......................... G06F 1/163
                                                          600/546
2014/0337861 A1* 11/2014 Chang ................... G06F 9/4843
                                                          719/313

* cited by examiner

*Primary Examiner* — Gerald Johnson
(74) *Attorney, Agent, or Firm* — Seed IP Law Group PLLC

(57) ABSTRACT

Systems, articles, and methods perform gesture identification with limited computational resources. A wearable electromyography ("EMG") device includes multiple EMG sensors, an on-board processor, and a non-transitory processor-readable memory that stores data and/or processor-executable instructions for performing gesture identification. The wearable EMG device detects and determines features of signals when a user performs a physical gesture, and processes the features by performing a decision tree analysis. The decision tree analysis invokes a decision tree stored in the memory, where storing and executing the decision tree may be managed by limited computational resources. The outcome of the decision tree analysis is a probability vector that assigns a respective probability score to each gesture in a gesture library. The accuracy of the gesture identification may be enhanced by performing multiple iterations of the decision tree analysis across multiple time windows of the EMG signal data and combining the resulting probability vectors.

27 Claims, 6 Drawing Sheets

SYSTEMS, ARTICLES, AND METHODS FOR GESTURE IDENTIFICATION IN WEARABLE ELECTROMYOGRAPHY DEVICES

BACKGROUND

1. Technical Field

The present systems, articles, and methods generally relate to wearable electromyography devices that perform automated gesture identification in real-time with limited computational resources.

2. Description of the Related Art

Wearable Electronic Devices

Electronic devices are commonplace throughout most of the world today. Advancements in integrated circuit technology have enabled the development of electronic devices that are sufficiently small and lightweight to be carried by the user. Such "portable" electronic devices may include on-board power supplies (such as batteries or other power storage systems) and may be designed to operate without any wire-connections to other electronic systems; however, a small and lightweight electronic device may still be considered portable even if it includes a wire-connection to another electronic system. For example, a microphone may be considered a portable electronic device whether it is operated wirelessly or through a wire-connection.

The convenience afforded by the portability of electronic devices has fostered a huge industry. Smartphones, audio players, laptop computers, tablet computers, and ebook readers are all examples of portable electronic devices. However, the convenience of being able to carry a portable electronic device has also introduced the inconvenience of having one's hand(s) encumbered by the device itself. This problem is addressed by making an electronic device not only portable, but wearable.

A wearable electronic device is any portable electronic device that a user can carry without physically grasping, clutching, or otherwise holding onto the device with their hands. For example, a wearable electronic device may be attached or coupled to the user by a strap or straps, a band or bands, a clip or clips, an adhesive, a pin and clasp, an article of clothing, tension or elastic support, an interference fit, an ergonomic form, etc. Examples of wearable electronic devices include digital wristwatches, electronic armbands, electronic rings, electronic ankle-bracelets or "anklets," head-mounted electronic display units, hearing aids, and so on.

Human-Electronics Interfaces

A wearable electronic device may provide direct functionality for a user (such as audio playback, data display, computing functions, etc.) or it may provide electronics to interact with, receive information from, or control another electronic device. For example, a wearable electronic device may include sensors that detect inputs effected by a user and transmit signals to another electronic device based on those inputs. Sensor-types and input-types may each take on a variety of forms, including but not limited to: tactile sensors (e.g., buttons, switches, touchpads, or keys) providing manual control, acoustic sensors providing voice-control, electromyography sensors providing gesture control, and/or accelerometers providing gesture control.

A human-computer interface ("HCI") is an example of a human-electronics interface. The present systems, articles, and methods may be applied to HCIs, but may also be applied to any other form of human-electronics interface.

Electromyography Devices

Electromyography ("EMG") is a process for detecting and processing the electrical signals generated by muscle activity. EMG devices employ EMG sensors that are responsive to the range of electrical potentials (typically μV-mV) involved in muscle activity. EMG signals may be used in a wide variety of applications, including: medical monitoring and diagnosis, muscle rehabilitation, exercise and training, prosthetic control, and even in controlling functions of electronic devices.

Human-electronics interfaces that employ EMG have been proposed. For example, U.S. Pat. No. 6,244,873 and U.S. Pat. No. 8,170,656 describe such systems. In a typical example, a user dons a wearable EMG device and performs physical gestures to control functions of a separate electronic device. EMG signals corresponding to each user-performed gesture are detected by the wearable EMG device and then either processed by the wearable EMG device itself using an on-board processor or transmitted to a separate computer system for processing. In either case, processing the EMG signals typically involves automatically identifying the corresponding gesture(s) performed by the user. It is advantageous to perform gesture identification on-board the wearable EMG device itself (i.e., using an on-board processor) because doing so enables a wider-range of electronic devices to be controlled.

Automated gesture identification based on EMG signal data is a challenging computational problem that employs techniques from the fields of pattern recognition, machine learning, and artificial intelligence. The algorithms involved typically include computationally intensive calculations such as non-linear optimizations, stochastic analyses, and so on. Such calculations can demand significant processing power, necessitating both a fast processor that is capable of performing such calculations in a reasonable amount of time and sufficient infrastructure to support the memory, electrical power, and cooling power requirements of the fast processor.

In a wearable electronic device, it is advantageous to minimize the total weight of the device and maximize the total battery life. Supporting a fast processor (and associated memory) that performs computationally intensive calculations on-board a wearable device can either require a bigger, heavier battery or significantly reduce the available battery life. A fast processor may also require a bulky cooling system. Furthermore, even with all of the support systems necessary to perform such computations on-board a wearable device, algorithms that involve computationally intensive calculations may still proceed unacceptably slowly for the purpose of real-time automated gesture identification in an HCI. There is a need in the art for wearable devices that can perform automated gesture identification in real-time using limited computational resources.

BRIEF SUMMARY

A method of operating a wearable electromyography ("EMG") device, wherein the wearable EMG device includes a set of EMG sensors and a processor communicatively coupled to the set of EMG sensors, may be summarized as including: detecting muscle activity of a user of the wearable EMG device by the set of EMG sensors, wherein the muscle activity corresponds to a user-performed gesture; in response to detecting muscle activity of the user by the set of EMG sensors, providing a set of signals from the set of EMG sensors to the processor; determining a set of features of the set of signals by the processor; performing a series of evaluations of at least some of the features in the set of features by the processor, wherein each evaluation in the series of evaluations includes evaluating a respective feature in the set of features by the processor, and wherein a first evaluation in the series of evaluations includes evaluating a first feature in the set of features by the processor and each subsequent evaluation in the series of evaluations is based at least in part on an outcome of a previous evaluation in the series of evaluations; determining a respective probability score of each gesture in a gesture library by the processor based at least in part on an outcome of the series of evaluations; and identifying the user-performed gesture by the processor based at least in part on the probability score of at least one gesture in the gesture library. Performing a series of evaluations of at least some of the features in the set of features by the processor may include performing a decision tree analysis of the set of features by the processor. Each evaluation in the series of evaluations may include comparing a magnitude of a respective feature in the set of features to a respective value by the processor. Determining a set of features of the set of signals by the processor may include determining at least one feature selected from the group consisting of: an average value of a signal in the set of signals, a mean value of a signal in the set of signals, a median value of a signal in the set of signals, a mode value of a signal in the set of signals, a maximum value of a signal in the set of signals, a minimum value of a signal in the set of signals, a standard deviation of a signal in the set of signals, and/or a root mean squared ("RMS") value of a signal in the set of signals.

Identifying the user-performed gesture by the processor based at least in part on the probability score of at least one gesture in the gesture library may include identifying, by the processor, a gesture in the gesture library that has a largest probability score. The wearable EMG device may further include a non-transitory processor-readable storage medium communicatively coupled to the processor, and wherein the non-transitory processor-readable storage medium stores processor-executable gesture identification instructions, and: determining a set of features of the set of signals by the processor may include executing, by the processor, the processor-executable gesture identification instructions to cause the processor to determine a set of features of the set of signals; performing a series of evaluations of at least some of the features in the set of features by the processor may include executing, by the processor, the processor-executable gesture identification instructions to cause the processor to perform a series of evaluations of at least some of the features in the set of features; determining a respective probability score of each gesture in a gesture library by the processor based at least in part on an outcome of the series of evaluations may include executing, by the processor, the processor-executable gesture identification instructions to cause the processor to determine a respective probability score of each gesture in a gesture library based at least in part on an outcome of the series of evaluations; and identifying the user-performed gesture by the processor based at least in part on the probability score of at least one gesture in the gesture library may include executing, by the processor, the processor-executable gesture identification instructions to cause the processor to identify the user-performed gesture based at least in part on the probability score of at least one gesture in the gesture library. The wearable EMG device may further include at least one inertial sensor, and the method may further include: detecting motion of the wearable EMG device by the at least one inertial sensor, wherein the motion corresponds to the user-performed gesture; in response to detecting motion of the wearable EMG device by the at least one inertial sensor, providing at least one signal from the at least one inertial sensor to the processor; and processing the at least one signal from the at least one inertial sensor by the processor, and wherein identifying the user-performed gesture by the processor based at least in part on the probability score of at least one gesture in the gesture library includes identifying the user-performed gesture by the processor based at least in part on an outcome of the processing the at least one signal from the at least one inertial sensor by the processor.

The method may include capturing a respective time-synchronized first portion of each signal in the set of signals by the processor, and: determining a set of features of the set of signals by the processor may include determining a set of features of the time-synchronized first portions of the signals in the set of signals by the processor; performing a series of evaluations of at least some of the features in the set of features by the processor may include performing a series of evaluations of at least some of the features of the time-synchronized first portions of the signals in the set of signals by the processor; and determining a respective probability score of each gesture in a gesture library by the processor based at least in part on an outcome of the series of evaluations may include determining a respective first probability score of each gesture in the gesture library by the processor based at least in part on an outcome of the series of evaluations of at least some of the features of the time-synchronized first portions of the signals in the set of signals. The method may further include capturing a respective time-synchronized second portion of each signal in the set of signals by the processor, wherein: determining a set of features of the set of signals by the processor includes determining a set of features of the time-synchronized second portions of the signals in the set of signals by the processor; performing a series of evaluations of at least some of the features in the set of features by the processor includes performing a series of evaluations of at least some of the features of the time-synchronized second portions of the signals in the set of signals by the processor; and determining a respective probability score of each gesture in a gesture library by the processor based at least in part on an outcome of the series of evaluations includes determining a respective second probability score of each gesture in the gesture library by the processor based at least in part on an outcome of the series of evaluations of at least some of the features of the time-synchronized second portions of the signals in the set of signals; and generating a respective cumulative probability score of each gesture in the gesture library by the processor, wherein the respective cumulative probability score of each gesture in the gesture library combines the first probability score of the gesture and the second probability score of the gesture, and wherein identifying the user-performed gesture by the processor based at least in part on the probability score of at least one gesture in the gesture library includes identifying the user-performed gesture by the processor based at least in part on the cumulative probability score of at least one gesture in the gesture library.

The method may include, in response to the user performing a reference gesture: determining an orientation of the wearable EMG device on the user by the wearable EMG device; and calibrating the series of evaluations by the wearable EMG device. Providing a set of signals from the set of EMG sensors to the processor may include providing a respective signal from each respective EMG sensor in the set of EMG sensors to the processor; and determining a set of features of the set of signals by the processor may include determining at least one respective feature of the signal from each respective EMG sensor in the set of EMG sensors by the processor. Determining a respective probability score of each gesture in a gesture library by the processor based at least in part on an outcome of the series of evaluations may include determining a corresponding probability vector from a set of probability vectors by the processor based at least in part on the outcome of the series of evaluations.

A wearable electromyography ("EMG") device may be summarized as including a set of EMG sensors responsive to muscle activity corresponding to a gesture performed by a user of the wearable EMG device, wherein in response to muscle activity corresponding to a gesture performed by the user, the set of EMG sensors provide a set of signals; a processor communicatively coupled to the set of EMG sensors; and a non-transitory processor-readable storage medium communicatively coupled to the processor, wherein the non-transitory processor-readable storage medium stores processor-executable gesture identification instructions that, when executed by the processor, cause the processor to: determine a set of features of the set of signals; perform a series of evaluations of at least some of the features in the set of features by the processor, wherein each evaluation in the series of evaluations includes evaluating a respective feature in the set of features, and wherein a first evaluation in the series of evaluations includes evaluating a first feature in the set of features and each subsequent evaluation in the series of evaluations is based at least in part on an outcome of a previous evaluation in the series of evaluations; determine a respective probability score of each gesture in a gesture library based at least in part on the series of evaluations; and identify the gesture performed by the user based at least in part on the probability score of at least one gesture in the gesture library. The device may include at least one communication terminal communicatively coupled to the processor, the at least one communication terminal to transmit information about the gesture performed by the user. The device may include at least one inertial sensor communicatively coupled to the processor, the at least one inertial sensor responsive to motion corresponding to the gesture performed by the user of the wearable EMG device, wherein in response to motion corresponding to the gesture performed by the user, the at least one inertial sensor provides at least one signal, and wherein the processor-executable gesture identification instructions that, when executed by the processor, cause the processor to identify the gesture performed by the user based at least in part on the probability score of at least one gesture in the gesture library cause the processor to identify the gesture performed by the user based at least in part on both the probability score of at least one gesture in the gesture library and the at least one signal provided by the at least one inertial sensor in response to the motion. The device may include a set of pod structures that form physically coupled links of the wearable EMG device, wherein each pod structure in the set of pod structures is positioned adjacent and in between two other pod structures in the set of pod structures and physically coupled to the two other pod structures in the set of pod structures, and wherein the set of pod structures forms a perimeter of an annular configuration.

A method of identifying a gesture performed by a user of a wearable EMG device, wherein the wearable EMG device includes a set of EMG sensors and a processor communicatively coupled to the set of EMG sensors, may be summarized as including: in response to the user performing a gesture while wearing the wearable EMG device, detecting muscle activity of the user by the set of EMG sensors; in response to detecting muscle activity of the user by the set of EMG sensors, providing a set of signals from the set of EMG sensors to the processor; determining a set of features of the set of signals by the processor; performing a decision tree analysis of the set of features by the processor; determining a respective probability score of each gesture in a gesture library by the processor based at least in part on an outcome of the decision tree analysis; and identifying the gesture performed by the user by the processor based at least in part on the probability score of at least one gesture in the gesture library. Performing a decision tree analysis of the set of features by the processor may include performing a series of evaluations of at least some of the features in the set of features by the processor, wherein each evaluation in the series of evaluations includes evaluating a respective feature in the set of features by the processor, and wherein a first evaluation in the series of evaluations includes evaluating a first feature in the set of features by the processor and each subsequent evaluation in the series of evaluations is based at least in part on an outcome of a previous evaluation in the series of evaluations. Each evaluation in the series of evaluations may include comparing a magnitude of a respective feature in the set of features to a respective value by the processor. Determining a set of features of the set of signals by the processor may include determining at least one feature selected from the group consisting of: an average value of a signal in the set of signals, a mean value of a signal in the set of signals, a median value of a signal in the set of signals, a mode value of a signal in the set of signals, a maximum value of a signal in the set of signals, a minimum value of a signal in the set of signals, a standard deviation of a signal in the set of signals, and/or a root mean squared ("RMS") value of a signal in the set of signals.

Identifying the gesture performed by the user by the processor based at least in part on the probability score of at least one gesture in the gesture library may include identifying, by the processor, a gesture in the gesture library that has a largest probability score. The device may include a non-transitory processor-readable storage medium communicatively coupled to the processor, wherein the non-transitory processor-readable storage medium stores processor-executable gesture identification instructions, and wherein: determining a set of features of the set of signals by the processor may include executing the processor-executable gesture identification instructions to cause the processor to determine a set of features of the set of signals; performing a decision tree analysis of the set of features by the processor may include executing the processor-executable gesture identification instructions to cause the processor to perform a decision tree analysis of the set of features; determining a respective probability score of each gesture in a gesture library by the processor based at least in part on an outcome of the decision tree analysis may include executing the processor-executable gesture identification instructions to cause the processor to determine a respective probability score of each gesture in a gesture library based at least in part on an outcome of the decision tree analysis; and identifying the gesture performed by the user by the processor based at least in part on the probability score of at least one gesture in the gesture library may include executing the processor-executable gesture identification instructions to cause the processor to identify the gesture performed by the user based at least in part on the probability score of at least one gesture in the gesture library. The device may include at least one inertial sensor, and the method may further include: in response to the user performing the gesture while wearing the wearable EMG device, detecting motion of the wearable EMG device by the at least one inertial sensor; in response to detecting motion of the wearable EMG device by the at least one inertial sensor, providing at least one signal from the at least one inertial sensor to the processor; and processing the at least one signal from the at least one inertial sensor by the processor, and wherein identifying the gesture performed by the user by the processor based at least in part on the probability score of at least one gesture in the gesture library includes identifying the gesture performed by the user by the processor based at least in part on a result of the processing the at least one signal from the at least one inertial sensor by the processor.

The method may include capturing a respective time-synchronized first portion of each signal in the set of signals by the processor, and: determining a set of features of the set of signals by the processor may include determining a set of features of the time-synchronized first portions of the signals in the set of signals by the processor; performing a decision tree analysis of the set of features by the processor may include performing a decision tree analysis of the set of features of the time-synchronized first portions of the signals in the set of signals by the processor; and determining a respective probability score of each gesture in a gesture library by the processor based at least in part on an outcome of the decision tree analysis may include determining a respective first probability score of each gesture in the gesture library by the processor based at least in part on an outcome of the decision tree analysis of the features of the time-synchronized first portions of the signals in the set of signals. The method may include: capturing a respective time-synchronized second portion of each signal in the set of signals by the processor, wherein: determining a set of features of the set of signals by the processor includes determining a set of features of the time-synchronized second portions of the signals in the set of signals by the processor; performing a decision tree analysis of the set of features by the processor includes performing a decision tree analysis of the set of features of the time-synchronized second portions of the signals in the set of signals by the processor; and determining a respective probability score of each gesture in a gesture library by the processor based at least in part on an outcome of the series of evaluations includes determining a respective second probability score of each gesture in the gesture library by the processor based at least in part on an outcome of the decision tree analysis of the features of the time-synchronized second portions of the signals in the set of signals; and generating a respective cumulative probability score of each gesture in the gesture library by the processor, wherein the respective cumulative probability score of each gesture in the gesture library combines the first probability score of the gesture and the second probability score of the gesture, and wherein identifying the user-performed gesture by the processor based at least in part on the probability score of at least one gesture in the gesture library includes identifying the user-performed gesture by the processor based at least in part on the cumulative probability score of at least one gesture in the gesture library.

The method may include, in response to the user performing a reference gesture: determining an orientation of the wearable EMG device on the user by the wearable EMG device; and calibrating the decision tree analysis of the wearable EMG device. Providing a set of signals from the set of EMG sensors to the processor may include providing a respective signal from each respective EMG sensor in the set of EMG sensors to the processor; and determining a set of features of the set of signals by the processor may include determining at least one respective feature of the signal from each respective EMG sensor in the set of EMG sensors by the processor. Determining a respective probability score of each gesture in a gesture library by the processor based at least in part on an outcome of the decision tree analysis may include determining a corresponding probability vector from a set of probability vectors by the processor based at least in part on the outcome of the decision tree analysis.

A wearable EMG device may be summarized as including: a set of EMG sensors responsive to muscle activity corresponding to a gesture performed by a user of the wearable EMG device, wherein in response to muscle activity corresponding to a gesture performed by the user, the set of EMG sensors provide a set of signals; a processor communicatively coupled to the set of EMG sensors; and a non-transitory processor-readable storage medium communicatively coupled to the processor, wherein the non-transitory processor-readable storage medium stores processor-executable gesture identification instructions that, when executed by the processor, cause the processor to: determine a set of features of the set of signals; perform a decision tree analysis of the set of features; determine a respective probability score of each gesture in a gesture library based at least in part on an outcome of the decision tree analysis; and identify the gesture performed by the user based at least in part on the probability score of at least one gesture in the gesture library. The device may include: at least one communication terminal communicatively coupled to the processor, the at least one communication terminal to transmit information about the gesture performed by the user. The device may include: at least one inertial sensor communicatively coupled to the processor, the at least one inertial sensor responsive to motion corresponding to the gesture performed by the user of the wearable EMG device, wherein in response to motion corresponding to the gesture performed by the user, the at least one inertial sensor provides at least one signal, and wherein the processor-executable gesture identification instructions that, when executed by the processor, cause the processor to identify the gesture performed by the user based at least in part on the probability score of at least one gesture in the gesture library cause the processor to identify the gesture performed by the user based at least in part on both the probability score of at least one gesture in the gesture library and the at least one signal provided by the at least one inertial sensor in response to the motion. The device may include a set of pod structures that form physically coupled links of the wearable EMG device, wherein each pod structure in the set of pod structures is positioned adjacent and in between two other pod structures in the set of pod structures and physically coupled to the two other pod structures in the set of pod structures, and wherein the set of pod structures forms a perimeter of an annular configuration.

A method of identifying which gesture in a gesture library is performed by a user of a wearable EMG device, wherein the wearable EMG device includes a set of EMG sensors and a processor communicatively coupled to the set of EMG sensors, may be summarized as including: in response to the user performing a gesture while wearing the wearable EMG device, detecting muscle activity of the user by the set of EMG sensors; in response to detecting muscle activity of the user by the set of EMG sensors, providing a set of signals from the set of EMG sensors to the processor, wherein each signal in the set of signals is provided by a respective one of the EMG sensors in the set of EMG sensors; until a cumulative probability score that exceeds a threshold value is identified, iteratively: capturing a respective time-synchronized portion of each signal in the set of signals by the processor; determining a set of features of the time-synchronized portions of the signals in the set of signals by the processor; performing a decision tree analysis of the set of features by the processor; determining a respective probability score of each gesture in the gesture library by the processor; generating a respective cumulative probability score of each gesture in the gesture library by the processor; and comparing the cumulative probability scores in the set of cumulative probability scores to the threshold value by the processor; and in response to identifying a cumulative probability score that exceeds a threshold value: stopping the iteration; and returning a gesture in the gesture library that corresponds to the cumulative probability score that exceeds the threshold value by the processor. Determining a set of features of the time-synchronized portions of the signals in the set of signals by the processor may include determining at least one respective feature of the time-synchronized portion of each respective signal in the set of signals by the processor. Performing a decision tree analysis of the set of features by the processor may include performing a series of evaluations of at least some of the features in the set of features by the processor, wherein each evaluation in the series of evaluations includes evaluating a respective feature in the set of features by the processor, and wherein a first evaluation in the series of evaluations includes evaluating a first feature in the set of features by the processor and each subsequent evaluation in the series of evaluations is based at least in part on an outcome of a previous evaluation in the series of evaluations. The wearable EMG device may further include at least one inertial sensor communicatively coupled to the processor, and the method may include: in response to the user performing the gesture while wearing the wearable EMG device, detecting motion of the wearable EMG device by the at least one inertial sensor; in response to detecting motion of the wearable EMG device by the at least one inertial sensor, providing at least one signal from the at least one inertial sensor to the processor; processing the at least one signal from the at least one inertial sensor by the processor; and identifying which gesture from the gesture library is performed by the user based at least in part on both the gesture in the gesture library that corresponds to the cumulative probability score that exceeds the threshold value and the processing the at least one signal from the at least one inertial sensor. Generating a respective cumulative probability score of each gesture in the gesture library by the processor may include, for each gesture in the gesture library, combining the respective probability scores from multiple iterations. Generating a respective cumulative probability score of each gesture in the gesture library in an $i^{th}$ iteration may include, for each gesture in the gesture library, combining the respective probability score determined in the $i^{th}$ iteration with the respective probability score determined in an $(i-1)^{th}$ iteration. Determining a respective probability score of each gesture in the gesture library by the processor may include determining a corresponding probability vector from a set of probability vectors by the processor based at least in part on an outcome of the decision tree analysis.

A wearable EMG device may be summarized as including: a set of EMG sensors responsive to muscle activity corresponding to a gesture performed by a user of the wearable EMG device, wherein in response to muscle activity corresponding to a gesture performed by the user, the set of EMG sensors provide a set of signals; a processor communicatively coupled to the set of EMG sensors; and a non-transitory processor-readable storage medium communicatively coupled to the processor, wherein the non-transitory processor-readable storage medium stores processor-executable gesture identification instructions that, when executed by the processor, cause the processor to: i) until a cumulative probability score that exceeds a threshold value is identified, iteratively: capture a respective time-synchronized portion of each signal in the set of signals; determine a set of features of the time-synchronized portions of the signals in the set of signals; perform a decision tree analysis of the set of features; determine a respective probability score of each gesture in the gesture library; generate a respective cumulative probability score of each gesture in the gesture library; and compare the cumulative probability scores in the set of cumulative probability scores to the threshold value; and ii) in response to identifying a cumulative probability score that exceeds a threshold value: stop the iteration; and return the gesture in the gesture library that corresponds to the cumulative probability score that exceeds the threshold value. The device may include at least one communication terminal communicatively coupled to the processor, the at least one communication terminal to transmit information about the gesture performed by the user. The device may include at least one inertial sensor communicatively coupled to the processor, the at least one inertial sensor responsive to motion corresponding to the gesture performed by the user of the wearable EMG device, wherein in response to motion corresponding to the gesture performed by the user, the at least one inertial sensor provides at least one signal, and wherein the processor-executable gesture identification instructions, when executed by the processor, cause the processor to identify the gesture performed by the user based at least in part on the at least one signal provided by the at least one inertial sensor in response to the motion. The device may include a set of pod structures that form physically coupled links of the wearable EMG device, wherein each pod structure in the set of pod structures is positioned adjacent and in between two other pod structures in the set of pod structures and physically coupled to the two other pod structures in the set of pod structures, and wherein the set of pod structures forms a perimeter of an annular configuration.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with electronic devices, and in particular portable electronic devices such as wearable electronic devices, have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its broadest sense, that is as meaning "and/or" unless the content clearly dictates otherwise.

The headings and Abstract of the Disclosure provided herein are for convenience only and do not interpret the scope or meaning of the embodiments.

The various embodiments described herein provide systems, articles, and methods for performing automated gesture identification in real-time using at least one wearable EMG device. Each example of a wearable EMG device described herein performs reliable, accurate and robust real-time gesture identification using limited computational resources, which provides numerous benefits including without limitation: extending the battery life of the device, enhancing the speed of the gesture identification process, simplifying the on-board processor and associated infrastructure, reducing the cost of the device, and reducing the overall mass and complexity of the device.

Throughout this specification and the appended claims, the term "gesture" is used to generally refer to a physical action (e.g., a movement, a stretch, a flex, a pose, etc.) performed or otherwise effected by a user. Any physical action performed or otherwise effected by a user that involves detectable muscle activity (detectable, e.g., by at least one appropriately positioned EMG sensor) and/or detectable motion (detectable, e.g., by at least one appropriately positioned inertial sensor, such as an accelerometer and/or a gyroscope) may constitute a gesture in the present systems, articles, and methods.

Figure 1:
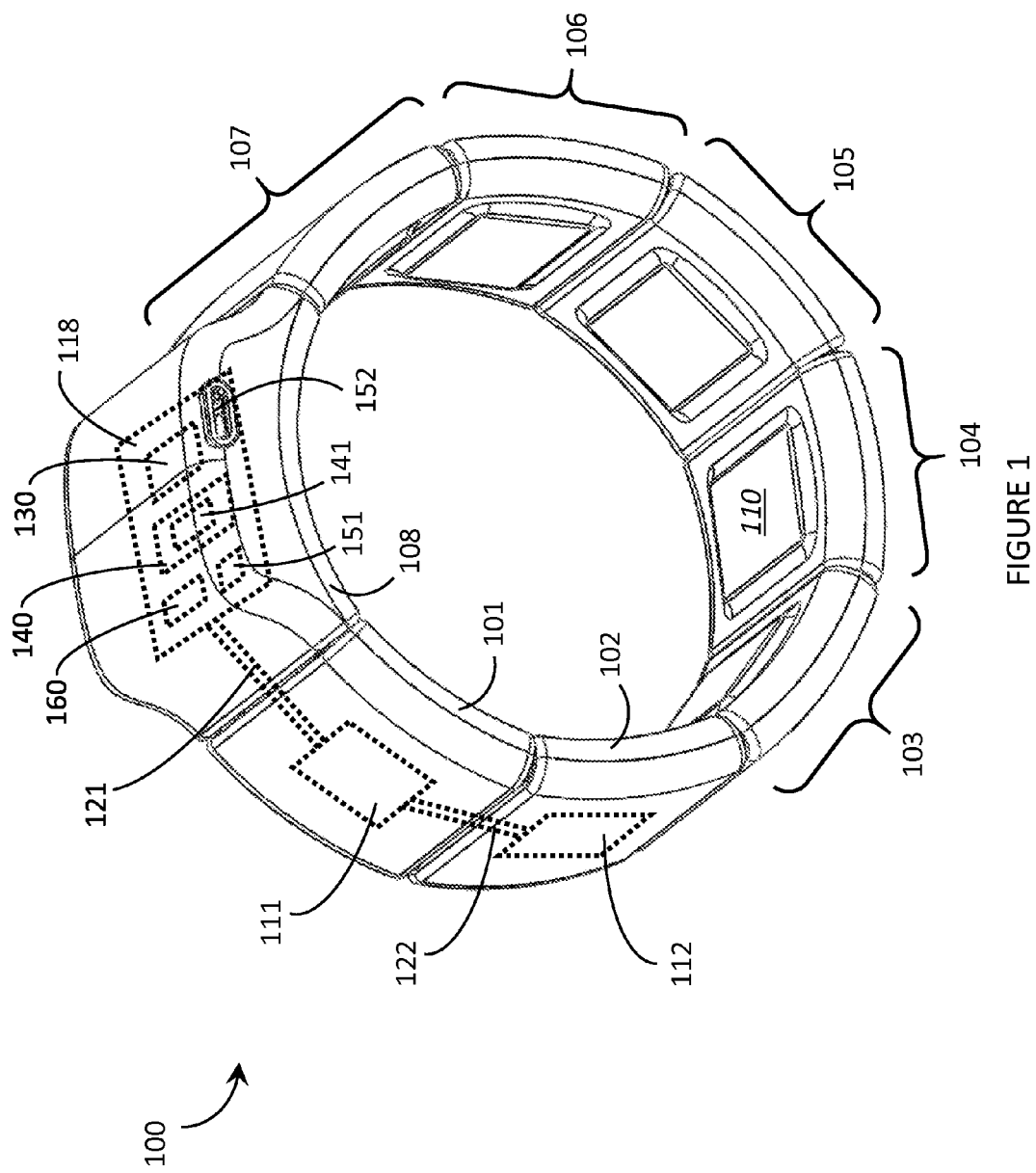
FIG. 1 is a perspective view of an exemplary wearable EMG device that performs gesture identification with limited computational resources in accordance with the present systems, articles, and methods.

FIG. 1 is a perspective view of an exemplary wearable EMG device 100 that performs gesture identification with limited computational resources in accordance with the present systems, articles, and methods. Exemplary wearable EMG device 100 may, for example, form part of a human-electronics interface. Exemplary wearable EMG device 100 is an armband designed to be worn on the forearm of a user, though a person of skill in the art will appreciate that the teachings described herein may readily be applied in wearable EMG devices designed to be worn elsewhere on the body of the user, including without limitation: on the upper arm, wrist, hand, finger, leg, foot, torso, or neck of the user. Some details of exemplary wearable EMG device 100 are described in at least U.S. Provisional Patent Application Ser. No. 61/752,226 (now U.S. Non-Provisional patent application Ser. No. 14/155,107), U.S. Provisional Patent Application Ser. No. 61/768,322 (now U.S. Non-Provisional patent application Ser. No. 14/186,889), U.S. Provisional Patent Application Ser. No. 61/771,500 (now U.S. Non-Provisional patent application Ser. No. 14/194,252), and U.S. Provisional Patent Application Ser. No. 61/869,526 (now U.S. Non-Provisional patent application Ser. No. 14/465,194), each of which is incorporated herein by reference in its entirety.

Device 100 includes a set of eight pod structures 101, 102, 103, 104, 105, 106, 107, and 108 that form physically coupled links of the wearable EMG device 100. Each pod structure in the set of eight pod structures 101, 102, 103, 104, 105, 106, 107, and 108 is positioned adjacent and in between two other pod structures in the set of eight pod structures such that the set of pod structures forms a perimeter of an annular or closed loop configuration. For example, pod structure 101 is positioned adjacent and in between pod structures 102 and 108 at least approximately on a perimeter of the annular or closed loop configuration of pod structures, pod structure 102 is positioned adjacent and in between pod structures 101 and 103 at least approximately on the perimeter of the annular or closed loop configuration, pod structure 103 is positioned adjacent and in between pod structures 102 and 104 at least approximately on the perimeter of the annular or closed loop configuration, and so on. Each of pod structures 101, 102, 103, 104, 105, 106, 107, and 108 is physically coupled to the two adjacent pod structures by at least one adaptive coupler (not visible in FIG. 1). For example, pod structure 101 is physically coupled to pod structure 108 by an adaptive coupler and to pod structure 102 by an adaptive coupler. The term "adaptive coupler" is used throughout this specification and the appended claims to denote a system, article or device that provides flexible, adjustable, modifiable, extendable, extensible, or otherwise "adaptive" physical coupling. Adaptive coupling is physical coupling between two objects that permits limited motion of the two objects relative to one another. An example of an adaptive coupler is an elastic material such as an elastic band. Thus, each of pod structures 101, 102, 103, 104, 105, 106, 107, and 108 in the set of eight pod structures may be adaptively physically coupled to the two adjacent pod structures by at least one elastic band. The set of eight pod structures may be physically bound in the annular or closed loop configuration by a single elastic band that couples over or through all pod structures or by multiple separate elastic bands that couple between adjacent pairs of pod structures or between groups of adjacent pairs of pod structures. Device 100 is depicted in FIG. 1 with the at least one adaptive coupler completely retracted and contained within the eight pod structures 101, 102, 103, 104, 105, 106, 107, and 108 (and therefore the at least one adaptive coupler is not visible in FIG. 1). Further details of adaptive coupling in wearable electronic devices are described in, for example, U.S. Provisional Application Ser. No. 61/860,063 (now U.S. Non-Provisional patent application Ser. No. 14/276,575), which is incorporated herein by reference in its entirety.

Throughout this specification and the appended claims, the term "pod structure" is used to refer to an individual link, segment, pod, section, structure, component, etc. of a wearable EMG device. For the purposes of the present systems, articles, and methods, an "individual link, segment, pod, section, structure, component, etc." (i.e., a "pod structure") of a wearable EMG device is characterized by its ability to be moved or displaced relative to another link, segment, pod, section, structure component, etc. of the wearable EMG device. For example, pod structures 101 and 102 of device 100 can each be moved or displaced relative to one another within the constraints imposed by the adaptive coupler providing adaptive physical coupling therebetween. The desire for pod structures 101 and 102 to be movable/displaceable relative to one another specifically arises because device 100 is a wearable EMG device that advantageously accommodates the movements of a user and/or different user forms.

Device 100 includes eight pod structures 101, 102, 103, 104, 105, 106, 107, and 108 that form physically coupled links thereof. Wearable EMG devices employing pod structures (e.g., device 100) are used herein as exemplary wearable EMG device designs, while the present systems, articles, and methods may be applied to wearable EMG devices that do not employ pod structures (or that employ any number of pod structures). Thus, throughout this specification, descriptions relating to pod structures (e.g., functions and/or components of pod structures) should be interpreted as being applicable to any wearable EMG device design, even wearable EMG device designs that do not employ pod structures (except in cases where a pod structure is specifically recited in a claim).

In exemplary device 100 of FIG. 1, each of pod structures 101, 102, 103, 104, 105, 106, 107, and 108 comprises a respective housing having a respective inner volume. Each housing may be formed of substantially rigid material and may be optically opaque. Throughout this specification and the appended claims, the term "rigid" as in, for example, "substantially rigid material," is used to describe a material that has an inherent tendency to maintain or restore its shape and resist malformation/deformation under the moderate stresses and strains typically encountered by a wearable electronic device.

Details of the components contained within the housings (i.e., within the inner volumes of the housings) of pod structures 101, 102, 103, 104, 105, 106, 107, and 108 are not visible in FIG. 1. To facilitate descriptions of exemplary device 100, some internal components are depicted by dashed lines in FIG. 1 to indicate that these components are contained in the inner volume(s) of housings and may not normally be actually visible in the view depicted in FIG. 1, unless a transparent or translucent material is employed to form the housings. For example, any or all of pod structures 101, 102, 103, 104, 105, 106, 107, and/or 108 may include circuitry (i.e., electrical and/or electronic circuitry). In FIG. 1, a first pod structure 101 is shown containing circuitry 111 (i.e., circuitry 111 is contained in the inner volume of the housing of pod structure 101), a second pod structure 102 is shown containing circuitry 112, and a third pod structure 108 is shown containing circuitry 118. The circuitry in any or all pod structures may be communicatively coupled to the circuitry in at least one other pod structure by at least one communicative pathway (e.g., by at least one electrically conductive pathway and/or by at least one optical pathway). For example, FIG. 1 shows a first set of communicative pathways 121 providing communicative coupling between circuitry 118 of pod structure 108 and circuitry 111 of pod structure 101, and a second set of communicative pathways 122 providing communicative coupling between circuitry 111 of pod structure 101 and circuitry 112 of pod structure 102. Communicative coupling between circuitries of pod structures in device 100 may advantageously include systems, articles, and methods for stretchable printed circuit boards as described in U.S. Provisional Patent Application Ser. No. 61/872,569 (now U.S. Non-Provisional patent application Ser. No. 14/471,982), systems, articles, and methods for signal routing as described in U.S. Provisional Patent Application Ser. No. 61/866,960 (now U.S. Non-Provisional patent application Ser. No. 14/461,044), and/or systems, articles, and methods for strain mitigation as described in U.S. Provisional Patent Application Ser. No. 61/857,105 (now U.S. Non-Provisional patent application Ser. No. 14/335,668), all of which are incorporated by reference herein in their entirety.

Throughout this specification and the appended claims the term "communicative" as in "communicative pathway," "communicative coupling," and in variants such as "communicatively coupled," is generally used to refer to any engineered arrangement for transferring and/or exchanging information. Exemplary communicative pathways include, but are not limited to, electrically conductive pathways (e.g., electrically conductive wires, electrically conductive traces), magnetic pathways (e.g., magnetic media), and/or optical pathways (e.g., optical fiber), and exemplary communicative couplings include, but are not limited to, electrical couplings, magnetic couplings, and/or optical couplings.

Each individual pod structure within a wearable EMG device may perform a particular function, or particular functions. For example, in device 100, each of pod structures 101, 102, 103, 104, 105, 106, and 107 includes a respective EMG sensor 110 (only one called out in FIG. 1 to reduce clutter) responsive to (i.e., to detect, measure, transduce, or otherwise respond to) muscle activity of a user and to provide electrical signals in response to the muscle activity. Thus, each of pod structures 101, 102, 103, 104, 105, 106, and 107 may be referred to as a respective "sensor pod." Throughout this specification and the appended claims, the term "sensor pod" is used to denote an individual pod structure that includes at least one sensor responsive to muscle activity of a user. Each EMG sensor 110 may be, for example, a respective capacitive EMG sensor that detects electrical signals generated by muscle activity through capacitive coupling, such as the capacitive EMG sensor described in U.S. Provisional Patent Application Ser. No. 61/771,500 (now Ser. No. 14/194,252).

Pod structure 108 of device 100 includes a processor 130 that processes the signals provided by the EMG sensors 110 of sensor pods 101, 102, 103, 104, 105, 106, and 107 in response to detected muscle activity. Pod structure 108 may therefore be referred to as a "processor pod." Throughout this specification and the appended claims, the term "processor pod" is used to denote an individual pod structure that includes at least one processor to process signals. The processor may be any type of processor, including but not limited to: a digital microprocessor or microcontroller, an application-specific integrated circuit (ASIC), a field-programmable gate array (FPGA), a digital signal processor (DSP), a graphics processing unit (GPU), a programmable gate array (PGA), a programmable logic unit (PLU), or the like, that analyzes or otherwise processes the signals to determine at least one output, action, or function based on the signals. A person of skill in the art will appreciate that implementations that employ a digital processor (e.g., a digital microprocessor or microcontroller, a DSP, etc.) may advantageously include a non-transitory processor-readable storage medium or memory communicatively coupled thereto and storing processor-executable instructions that control the operations thereof, whereas implementations that employ an ASIC, FPGA, or analog processor may or may not include a non-transitory processor-readable storage medium.

As used throughout this specification and the appended claims, the terms "sensor pod" and "processor pod" are not necessarily exclusive. A single pod structure may satisfy the definitions of both a "sensor pod" and a "processor pod" and may be referred to as either type of pod structure. For greater clarity, the term "sensor pod" is used to refer to any pod structure that includes a sensor and performs at least the function(s) of a sensor pod, and the term processor pod is used to refer to any pod structure that includes a processor and performs at least the function(s) of a processor pod. In device 100, processor pod 108 includes an EMG sensor 110 (not visible in FIG. 1) to sense, measure, transduce or otherwise detect muscle activity of a user, so processor pod 108 could be referred to as a sensor pod. However, in exemplary device 100, processor pod 108 is the only pod structure that includes a processor 130, thus processor pod 108 is the only pod structure in exemplary device 100 that can be referred to as a processor pod. The processor 130 in processor pod 108 also processes the EMG signals provided by the EMG sensor 110 of processor pod 108. In alternative embodiments of device 100, multiple pod structures may include processors, and thus multiple pod structures may serve as processor pods. Similarly, some pod structures may not include sensors, and/or some sensors and/or processors may be laid out in other configurations that do not involve pod structures.

In device 100, processor 130 includes and/or is communicatively coupled to a non-transitory processor-readable storage medium or memory 140. As will be described in more detail later, memory 140 may store data and/or processor-executable gesture identification instructions 141 that, when executed by processor 130, cause processor 130 to process the EMG signals from EMG sensors 110 and identify a gesture to which the EMG signals correspond. For communicating with a separate electronic device (not shown), wearable EMG device 100 includes at least one communication terminal communicatively coupled to processor 130. Throughout this specification and the appended claims, the term "communication terminal" is generally used to refer to any physical structure that provides a telecommunications link through which a data signal may enter and/or leave a device. A communication terminal represents the end (or "terminus") of communicative signal transfer within a device and the beginning of communicative signal transfer to/from an external device (or external devices). As examples, device 100 includes a first communication terminal 151 and a second communication terminal 152. First communication terminal 151 includes a wireless transmitter (i.e., a wireless communication terminal) and second communication terminal 152 includes a tethered connector port 152. Wireless transmitter 151 may include, for example, a Bluetooth® transmitter (or similar) and connector port 152 may include a Universal Serial Bus port, a mini-Universal Serial Bus port, a micro-Universal Serial Bus port, a SMA port, a THUNDERBOLT® port, or the like.

For some applications, device 100 may also include at least one inertial sensor 160 (e.g., an inertial measurement unit, or "IMU," that includes at least one accelerometer and/or at least one gyroscope) responsive to (i.e., detect, sense, transduce, measure, or otherwise respond to) motion effected by a user and provide signals in response to the motion. As will be described in more detail later, signals provided by inertial sensor 160 may be combined or otherwise processed in conjunction with signals provided by EMG sensors 110.

Throughout this specification and the appended claims, the term "provide" and variants such as "provided" and "providing" are frequently used in the context of signals. For example, an EMG sensor is described as "providing at least one signal" and an inertial sensor is described as "providing at least one signal." Unless the specific context requires otherwise, the term "provide" is used in a most general sense to cover any form of providing a signal, including but not limited to: relaying a signal, outputting a signal, generating a signal, routing a signal, creating a signal, transducing a signal, and so on. For example, a capacitive EMG sensor may include at least one electrode that capacitively couples to electrical signals from muscle activity. This capacitive coupling induces a change in a charge or electrical potential of the at least one electrode which is then relayed through the sensor circuitry and output, or "provided," by the sensor. Thus, the capacitive EMG sensor may "provide" an electrical signal by relaying an electrical signal from a muscle (or muscles) to an output (or outputs). In contrast, an inertial sensor may include components (e.g., piezoelectric, piezoresistive, capacitive, etc.) that are used to convert physical motion into electrical signals. The inertial sensor may "provide" an electrical signal by detecting motion and generating an electrical signal in response to the motion.

As previously described, each of pod structures 101, 102, 103, 104, 105, 106, 107, and 108 may include circuitry (i.e., electrical and/or electronic circuitry). FIG. 1 depicts circuitry 111 inside the inner volume of sensor pod 101, circuitry 112 inside the inner volume of sensor pod 102, and circuitry 118 inside the inner volume of processor pod 118. The circuitry in any or all of pod structures 101, 102, 103, 104, 105, 106, 107 and 108 (including circuitries 111, 112, and 118) may include any or all of: an amplification circuit to amplify electrical signals provided by at least one EMG sensor 110, a filtering circuit to remove unwanted signal frequencies from the signals provided by at least one EMG sensor 110, and/or an analog-to-digital conversion circuit to convert analog signals into digital signals. Device 100 may also include at least one battery (not shown in FIG. 1) to provide a portable power source for device 100.

Signals that are provided by EMG sensors 110 in device 100 are routed to processor pod 108 for processing by processor 130. To this end, device 100 employs a set of communicative pathways (e.g., 121 and 122) to route the signals that are output by sensor pods 101, 102, 103, 104, 105, 106, and 107 to processor pod 108. Each respective pod structure 101, 102, 103, 104, 105, 106, 107, and 108 in device 100 is communicatively coupled to, over, or through at least one of the two other pod structures between which the respective pod structure is positioned by at least one respective communicative pathway from the set of communicative pathways. Each communicative pathway (e.g., 121 and 122) may be realized in any communicative form, including but not limited to: electrically conductive wires or cables, ribbon cables, fiber-optic cables, optical/photonic waveguides, electrically conductive traces carried by a rigid printed circuit board, electrically conductive traces carried by a flexible printed circuit board, and/or electrically conductive traces carried by a stretchable printed circuit board.

Device 100 from FIG. 1 represents an example of a wearable EMG device that incorporates the teachings of the present systems, articles, and methods, though the teachings of the present systems, articles, and methods are applicable to any wearable EMG device that includes at least one EMG sensor (or more generally, to any gesture-based control device as discussed in more detail later on). In most applications, it is advantageous for the wearable EMG device to include an on-board processor for performing gesture identification as described herein, but a person of skill in the art will appreciate that at least some of the acts involved in gesture identification described herein may be performed by a processor that is separate from the wearable EMG device (e.g., a processor in a computer that receives signals from the wearable EMG device).

Throughout the descriptions of the systems, articles, and methods that follow, reference is made to the elements of system 100 from FIG. 1. A person of skill in the art will appreciate that the elements of system 100 are cited in relation to various systems, articles, and methods as illustrative examples only and that the various embodiments described herein may differ from the exemplary embodiment illustrated in FIG. 1. The scope of the present systems, articles, and methods should be construed based on the appended claims. For this reason, throughout the remainder of this description references to elements of system 100 from FIG. 1 are placed in parentheses to indicate that such references are non-limiting and used for illustrative purposes only.

The present systems, articles, and methods describe wearable EMG devices (e.g., 100) that perform automated gesture identification in real-time without invoking computationally intensive calculations that would demand a fast on-board processor and associated support infrastructure. The techniques for gesture identification described herein are specifically designed to be executed by a low-power, low-memory on-board processor in order to simplify the on-board gesture identification system(s) and/or sub-system(s) (e.g., processor 130, memory 140, and gesture identification instructions 141), their associated footprint(s) in the wearable EMG device (e.g., 100), and their associated resource demands.

Throughout this specification and the appended claims, the term "real-time" as in "gesture identification in real-time" is used to describe a data processing procedure that is executed and completed without any substantially perceivable delay. In the case of gesture identification in real-time, the term "real-time" is used to indicate that the gesture identification procedure is executed and completed without the user perceiving any substantial delay between performing the gesture and receiving feedback that the gesture has been identified. The nature of the feedback depends on the specific application, and may include, for example, execution of a function or operation in response to the user-performed gesture. In general, a user is expected to clearly perceive a delay if it's duration exceeds about two seconds and it is advantageous for "gesture identification in real-time" to be executed and completed within one second of the user performing a gesture.

The wearable EMG devices (e.g., 100) described herein include a non-transitory processor-readable storage medium (e.g., 140). The storage medium (e.g., 140) stores processor-executable gesture identification instructions (e.g., 141) that, when executed by the processor (e.g., 130) of the wearable EMG device (e.g., 100), cause the processor (e.g., 130) of the wearable EMG device (e.g., 100) to identify user-performed gestures using generalized algorithms that are substantially robust against variations in the specific use parameters (such as the form of the user, the orientation of the wearable EMG device, and/or environmental conditions).

Figure 2:
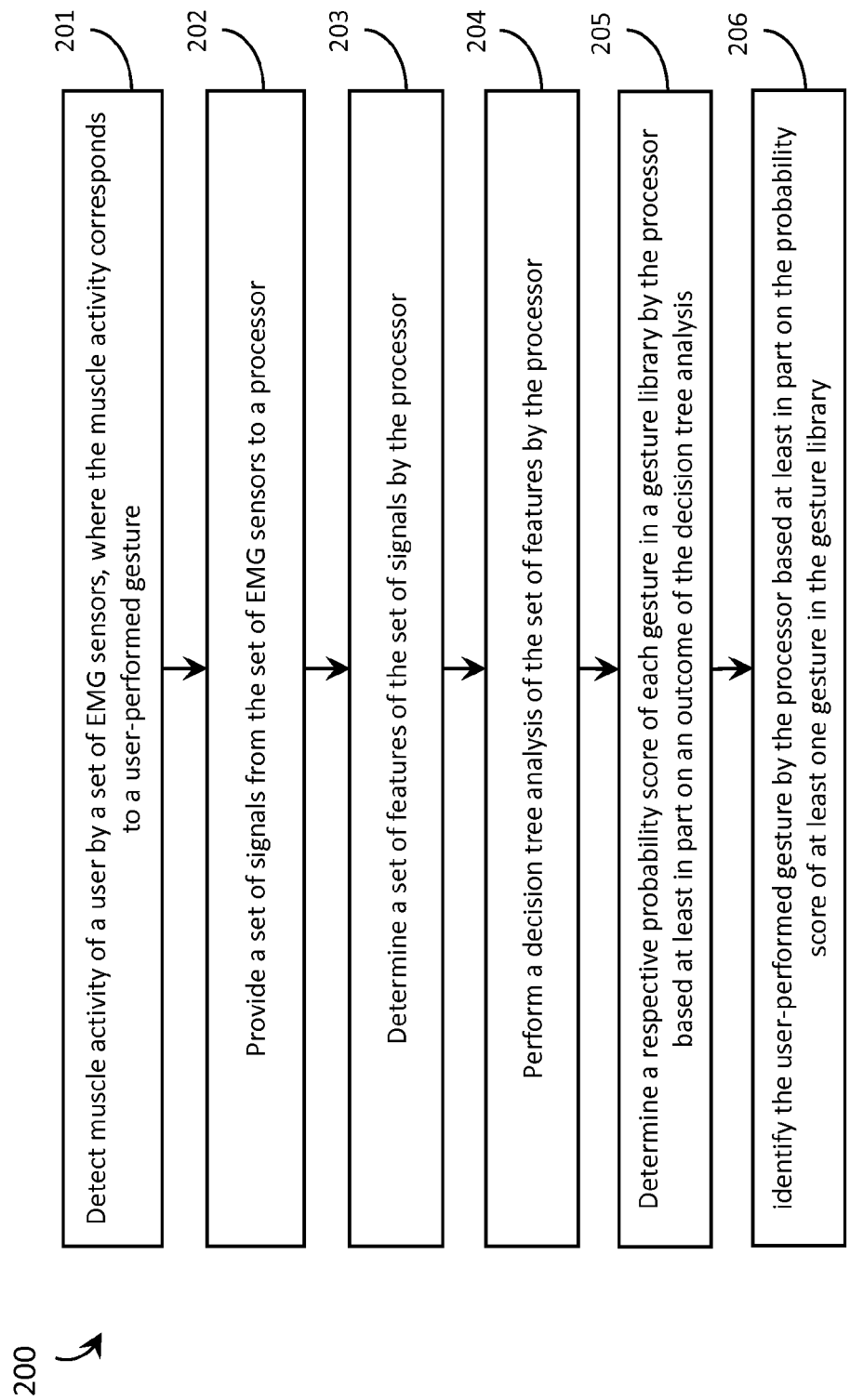
FIG. 2 is a flow-diagram showing a method of operating a wearable EMG device in accordance with the present systems, articles, and methods.

FIG. 2 is a flow-diagram showing a method 200 of operating a wearable EMG device (100) in accordance with the present systems, articles, and methods. More specifically, method 200 is a method of identifying a gesture performed by (e.g., identifying which gesture in a gesture library is performed by) a user of a wearable EMG device. The wearable EMG device (100) includes a set of EMG sensors (110) and a processor (130) and may form part of a human-electronics interface in which the wearable EMG device (100) is used to provide gesture-based interaction with and/or control of an electronic device.

Throughout this specification and the appended claims, "identifying" a gesture means associating a set of signals provided by one or more EMG sensor(s) (110) (and/or one or more other sensor(s), such as one or more inertial sensor(s)) with a gesture from a gesture library. In the various embodiments described herein, "identifying" a gesture includes determining which gesture in a gesture library is most probable (relative to the other gestures in the gesture library) of being the gesture that a user has performed or is performing in order to produce the signals upon which the gesture identification is at least partially based.

Method 200 includes six acts 201, 202, 203, 204, 205, and 206, though those of skill in the art will appreciate that in alternative embodiments certain acts may be omitted and/or additional acts may be added. Those of skill in the art will also appreciate that the illustrated order of the acts is shown for exemplary purposes only and may change in alternative embodiments. For the purpose of method 200, the term "user" refers to a person that is wearing the wearable EMG device (100).

At 201, a set of EMG sensors (110) detect muscle activity of a user of the wearable EMG device (100). The muscle activity corresponds to a user-performed gesture (i.e., a physical gesture that is performed by the user). As an example, the wearable EMG device (100) may be worn on an arm of the user and the physical gesture may include a hand gesture such as a finger extension, a pinching gesture, a finger snap, a clenched fist, etc. As previously described, the EMG sensors (110) may include, for example, capacitive EMG sensors that detect electrical signals generated by the user's muscle activity through capacitive coupling thereto.

At 202, the set of EMG sensors (110) provide a set of signals to the processor (130) of the wearable EMG device (100) in response to the detected muscle activity of act 201. The signals may be, for example, electrical or optical signals routed from the EMG sensors (110) to the processor (130) through electrically conductive or optical communicative pathways (121, 122). Providing a set of signals from the set of EMG sensors (110) to the processor (130) may include providing a respective signal from each respective EMG sensor (110) in the set of EMG sensors to the processor (130). For example, each EMG sensor (110) in the set of EMG sensors may communicatively couple to the processor (130) using a respective signal channel (121, 122) to provide either analog or digital signals to the processor (130) in response to detected muscle activity. In the case of providing analog signals from each EMG sensor (110) in the set of EMG sensors to the processor (130), a respective signal channel (121, 122) in the form of a respective physical communicative link (e.g., a respective signal line formed of one or more wires and/or one or more conductive traces, etc.) may communicatively couple from each EMG sensor (110) to the processor (130). In the case of providing digital signals from each EMG sensor (110) in the set of EMG sensors to the processor (130), each EMG sensor (110) may be allocated a respective effective signal channel in the form of, for example, a dedicated bit assignment (i.e., an allocation of bits in specific positions of a bit string), a dedicated signal or time window (i.e., with reference to a clock signal), etc. Further details of systems, articles, and methods for signal routing in wearable EMG devices are described in, for example, U.S. Provisional Patent Application Ser. No. 61/866,960 (now Ser. No. 14/461,044).

At 203, the processor (130) of the wearable EMG device (100) determines a set of features of the set of signals. The set of features may include characteristics, parameters, magnitudes, or generally any property or properties of the signals in the set of signals in the time, frequency, and/or time-frequency domains. Determining the set of features of the set of signals by the processor (130) may include determining a respective feature or respective features of each signal in the set of signals by the processor (130). The feature(s) that is/are determined for each signal by the processor (130) may include, without limitation: an average value of each signal in the set of signals, a mean value of each signal in the set of signals, a median value of each signal in the set of signals, a mode value of each signal in the set of signals, a maximum value of each signal in the set of signals, a minimum value of each signal in the set of signals, a standard deviation of each signal in the set of signals, and/or a root mean square ("RMS") value of each signal in the set of signals. The set of features determined at 203 may include the same type of feature or signal characteristic (e.g., magnitude, voltage, potential, amperage, state, direction) of each signal in the set of signals or may include different types of features or signal characteristics of different signals in the set of signals. The set of features determined at 203 may include the features themselves, or may include relationships between the features, such as respective differences between pairs of features, respective ratios of at least two features, and/or respective correlations between pairs of features. Relationships (e.g., differences, ratios, and/or correlations) between features may be determined by the processor (130) of the wearable EMG device (100).

As previously described, the wearable EMG device (100) may include a non-transitory processor-readable storage medium or memory (140) that is communicatively coupled to the processor (130), where the memory (140) stores processor-executable gesture identification instructions (141) that, when executed by the processor (130), cause the processor (130) to determine a set of features of the set of signals per act 203 of method 200.

At 204, the processor (130) of the wearable EMG device (100) performs a decision tree analysis of the set of features. The decision tree analysis may include, for example, performing a series of evaluations of at least some of the features in the set of features by the processor (130). Each evaluation in the series of evaluations may include evaluating a respective feature from the set of features by the processor (130). The series of evaluations may proceed according to a branching "tree" structure where the outcome of each evaluation determines whether or not a next evaluation will be performed and, if a next evaluation is to be performed, what the next evaluation will be. For example, a first evaluation in the series of evaluations may include evaluating a first feature from the set of features by the processor (130) and a "decision" to perform a second evaluation based on the outcome of the first evaluation. Each successive evaluation in the series of evaluations may be based at least in part on an outcome of a previous evaluation in the series of evaluations. Each evaluation in the series of evaluations may involve comparing a magnitude of a respective feature from the set of features to a respective value by the processor. Further details of decision tree structure are described later with reference to FIG. 3.

As previously described, the wearable EMG device (100) may include a non-transitory processor-readable storage medium or memory (140) that is communicatively coupled to the processor (130), where the memory (140) stores processor-executable gesture identification instructions (141) that, when executed by the processor (130), cause the processor to perform a decision tree analysis of the set of features (e.g., cause the processor to perform a series of evaluations of the set of features) per act 204 of method 200.

At 205, the processor (130) determines a respective probability score of each gesture in a gesture library based at least in part on an outcome of the decision tree analysis. Throughout this specification and the appended claims, the term "gesture library" is used to generally describe a set of gestures that a wearable EMG device (100) is operative to identify. The wearable EMG devices described herein are generally not operative to identify any arbitrary gesture performed by a user. Rather, the wearable EMG devices described herein are operative to identify when a user performs one of a specified set of gestures, and that specified set of gestures is referred to herein as a gesture library. A gesture library may include any number of gestures, though a person of skill in the art will appreciate that the precision/accuracy of gesture identification may be inversely related to the number of gestures in the gesture library. A gesture library may be expanded by adding one or more gesture(s) or reduced by removing one or more gesture(s). Furthermore, in accordance with the present systems, articles, and methods, a gesture library may include a "rest" gesture corresponding to a state for which no activity is detected and/or an "unknown" gesture corresponding to a state for which activity is detected but the processor determines that the activity does not correspond to any other gesture in the gesture library.

As will be described in more detail later (with reference to FIG. 3), the outcome of the decision tree analysis may be a set of numbers (e.g., a set of normalized numbers), referred to herein as a "probability vector," where each number in the set of numbers represents the probability that a respective gesture from the gesture library is the user-performed gesture. Thus, the decision tree analysis of act 204 receives the set of features of the set of EMG signals from act 203 as inputs and provides a probability vector as an output (i.e., as an outcome), where each element of the probability vector corresponds to the probability that a respective gesture from the gesture library has been performed. The number of entries in the probability vector corresponds to the number of gestures in the gesture library, and the sum of the entries in the probability vector is at least approximately equal to one (allowing for uncertainty in some analysis parameters). In some implementations, determining a respective probability score of each gesture in a gesture library at 204 may be considered as part of the decision tree analysis of act 203 (i.e., as an outcome of the decision tree analysis of act 203).

As previously described, the wearable EMG device (100) may include a non-transitory processor-readable storage medium or memory (140) that is communicatively coupled to the processor (130), where the memory (140) stores processor-executable gesture identification instructions (141) that, when executed by the processor (130), cause the processor (130) to determine a respective probability score of each gesture in a gesture library per act 204 of method 200 based at least in part on an outcome of the decision tree analysis of act 203.

At 206, the processor (130) determines, selects, or otherwise identifies the user-performed gesture based at least in part on the probability score of at least one gesture in the gesture library. For example, the processor (130) may identify the user-performed gesture as the gesture in the gesture library that has the largest probability score. In some implementations, the processor may compare the largest probability score to a threshold value and only identify the user-performed gesture as the gesture with the largest probability score if the largest probability score exceeds the threshold value. The threshold value may be set at any level depending on the implementation. For example, in applications where the gesture library is large and accurate gesture identification is very important (e.g., because each gesture controls a very different function), the threshold value may be set high (e.g., at 0.8, 0.9, or higher), whereas in applications that can tolerate more relaxed gesture identification (e.g., because there are few gestures and/or each gesture controls a similar function) the threshold value may be set low (e.g., at 0.7, 0.6, or lower).

In implementations where the wearable EMG device (100) includes a non-transitory processor-readable storage medium or memory (140) that is communicatively coupled to the processor (130), the memory (140) may store processor-executable gesture identification instructions (141) that, when executed by the processor (130), cause the processor (130) to identify the user-performed gesture based at least in part on the probability score of at least one gesture in the gesture library per act 206.

Method 200 may be implemented, executed, performed, or otherwise carried out by exemplary wearable EMG device 100 from FIG. 1, or more generally by any wearable EMG device that includes: a set of EMG sensors (110) responsive to (i.e., to detect) muscle activity corresponding to a gesture performed by a user of the wearable EMG device per act 201 and to, in response to such muscle activity, provide a set of signals per act 202; a processor (130) communicatively coupled to the set of EMG sensors (110); and a non-transitory processor-readable storage medium (140) communicatively coupled to the processor (130), where the non-transitory processor-readable storage medium (140) processor-executable gesture identification instructions (141) that, when executed by the processor (130), cause the processor (130) to: determine a set of features of the set of signals per act 203; perform a decision tree analysis (and/or a series of evaluations) of the set of features per act 204; determine a respective probability score of each gesture in a gesture library based at least in part on an outcome of the decision tree analysis per act 205; and determine, select or otherwise identify the gesture performed by the user based at least in part on the probability score of at least one gesture in the gesture library per act 206.

In accordance with the present systems, articles, and methods, information about a gesture library and/or the gestures included therein may be contained, encoded, or otherwise embodied in, for example, a decision tree, and/or in non-transitory processor-readable memory and/or processor-executable gesture identification instructions that embody a decision tree. As will be described in more detail later (specifically, in reference to FIG. 3), the various embodiments described herein do not require that any specific features, patterns, signatures, traits, characteristics, or other aspects of specific gestures (i.e., of the EMG signals that correspond to specific gestures) be identified, specified or defined and stored in a gesture library. For example, known proposals for automated gesture identification typically involve defining a unique signature or template for the EMG signals that correspond to each gesture in a gesture library (e.g., by employing pattern recognition techniques) and then matching a set of incoming EMG signals to one of the defined templates (e.g., by employing pattern matching techniques). Thus, known proposals for automated gesture identification may employ a gesture library in which each gesture is defined by a unique gesture pattern, gesture signature, gesture template, or similar, and may identify a user-performed gesture by matching the pattern, signature, template, or similar of the corresponding EMG signal data to the patterns, signatures, templates, or similar stored in the gesture library. The present systems, articles, and methods may not store any patterns, signatures, templates, or similar of the gestures in the gesture library, and may not identify a user-performed gesture by matching a pattern, signature, template, or similar of the corresponding EMG signal data to stored information in a gesture library. Rather, the present systems, articles, and methods may involve using techniques of machine learning to construct a decision tree based on a defined gesture library such that features of the gestures in the gesture library become contained, encoded, or otherwise embodied in the decision tree and the gesture library may manifest itself in the number of entries in the probability vector output by the decision tree and in the respective meaning of each entry in the probability vector.

Throughout this specification and the appended claims, reference is often made to a "decision tree" and a "decision tree analysis." A decision tree is known in the art as a predictive model which selectively maps a set of input data to one of a set of outputs based on a series of evaluations, classifications, and/or binary decisions. A "decision tree" is used herein as an example of a classifier that maps features of EMG signal data to probability scores of gestures in a gesture library, and in accordance with the present systems, articles and methods other forms of classifiers may similar be employed.

Figure 3:
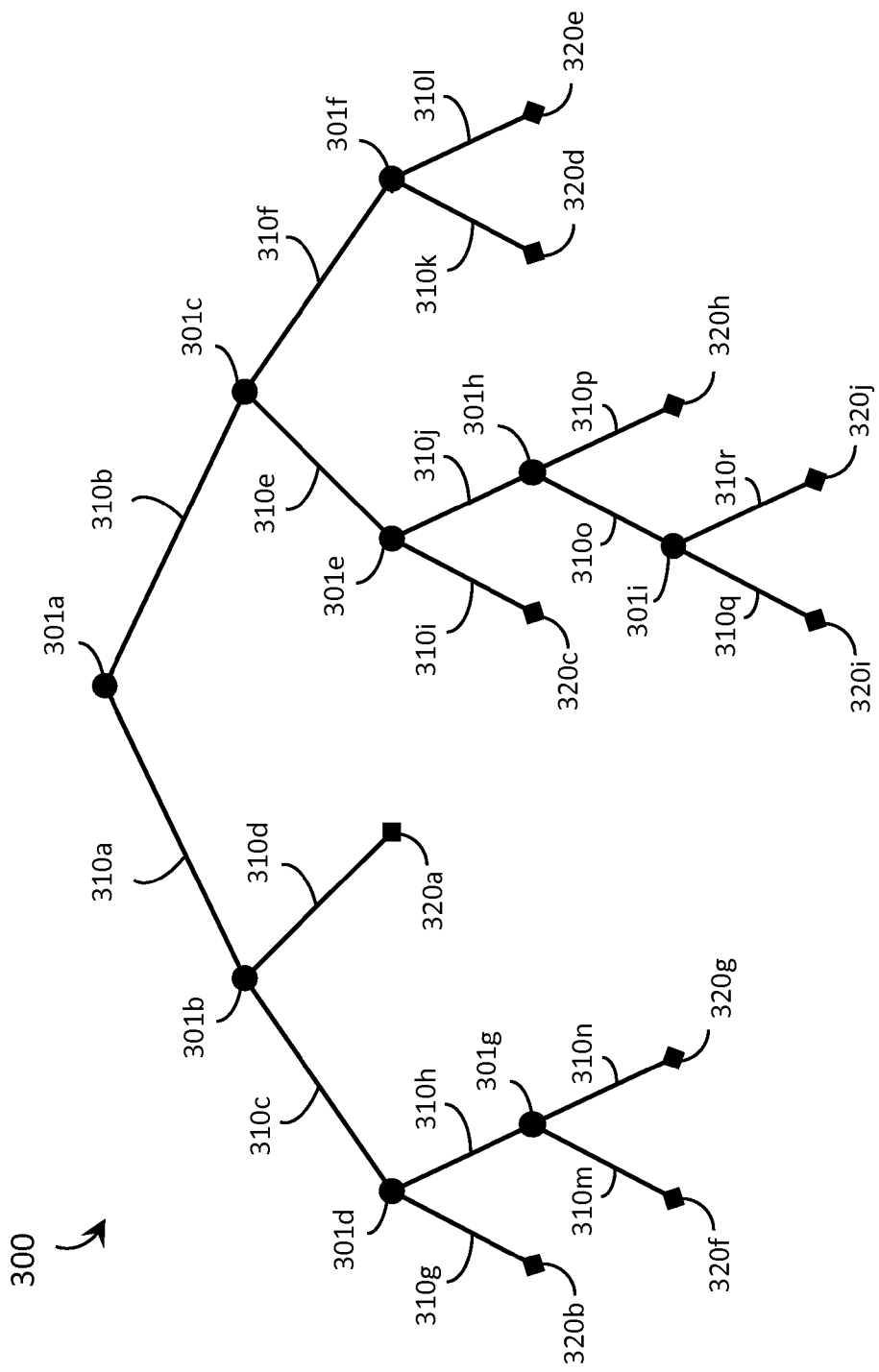
FIG. 3 is an illustrative diagram of an exemplary decision tree for use in performing a decision tree analysis of a set of EMG signal features as part of a gesture identification procedure in accordance with the present systems, articles, and methods.

FIG. 3 is an illustrative diagram of an exemplary decision tree 300 for use in performing a decision tree analysis of a set of EMG signal features as part of a gesture identification procedure (e.g., act 204 of method 200) in accordance with the present systems, articles, and methods. Decision tree 300 includes a set of decision nodes 301a-301i (collectively referred to as 301), a set of branches 310a-310r (collectively referred to as 310), and a set of leaf nodes 320a-320j (collectively referred to as 320). At each decision node 301, an input parameter (e.g., a feature from a set of EMG signal features) is evaluated by, for example, comparing a magnitude thereof to a value. The two branches 310 that extend downwards from each decision node 301 represent the two potential outcomes of such a comparison. For example, at decision node 301a, a magnitude of a first feature in a set of features is compared to a first value. If the magnitude of the first feature is, for example, greater than the first value, then the decision tree analysis may proceed along branch 310a to decision node 301b. If the magnitude of the first feature is, for example, less than or equal to the first value, then the decision tree analysis may proceed along branch 310b to decision node 301c. Thus, decision tree 300 represents a series of evaluations of at least some of the features in a set of features by a processor (130). A first evaluation in the series of evaluations (i.e., at decision node 301a) includes evaluating a first feature from the set of features by the processor (130), and each subsequent evaluation in the series of evaluations (i.e., decision nodes 301b-301i) is based at least in part on an outcome of a previous evaluation in the series of evaluations. Decision tree 300 terminates at a set of leaf nodes 320a-320j. Each leaf node 320 corresponds to a respective assignment of probability scores to the gestures in a gesture library. In other words, each leaf node 320 corresponds to a respective probability vector that may be returned by the processor (130) as an outcome of the decision tree analysis (e.g., per act 205 of method 200). Two exemplary instances of performing a decision tree analysis per act 204 of method 200 using decision tree 300 are now described.

At act 203 of method 200, a set of features of a set of EMG signals is determined by a processor (130). The set of features may comprise a set of numbers, where each number represents a characteristic or parameter obtained from the EMG signal data (e.g., a set of RMS values). Therefore, each feature in the set of features may have a corresponding magnitude. The set of features is provided as inputs to decision tree 300. At decision node 301a, a magnitude of a first feature in the set of features is compared to a first value.

In a first example, the magnitude of the first feature is greater than a magnitude of the first value. In this case, the decision tree analysis proceeds along branch 310a to decision node 301b. At decision node 301b, a magnitude of a second feature in the set of features is compared to a magnitude of a second value. In this first example, the magnitude of the second feature is greater than the magnitude of the second value, so the decision tree analysis proceeds along branch 310c to decision node 301d. At decision node 301d, a magnitude of a third feature in the set of features in compared to a magnitude of a third value. In this first example, the magnitude of the third feature is less than the magnitude of the third value, so the decision tree analysis proceeds along branch 310h to decision node 301g. At decision node 301g, a magnitude of a fourth feature in the set of features is compared to a magnitude of a fourth value. In this first example, the magnitude of the fourth feature is less than the magnitude of the fourth value, so the decision tree analysis proceeds along branch 310n to leaf node 320g. Leaf node 320g corresponds to a particular probability vector that assigns a particular respective probability score to each gesture in a gesture library. For example, the gesture library may include four gestures: "fist," "thumbs up," "point or gun," and "peace sign," and the probability vector of leaf node 320g may assign probability scores to these gestures as (0, 0.1, 0.3, 0.6), meaning that the outcome of the decision tree analysis determines that there is a 0% probability that the user-performed gesture is a "fist" gesture, a 10% probability that the user-performed gesture is a "thumbs up" gesture, a 30% probability that the user-performed gesture is a "point or gun" gesture, and a 60% probability that the user-performed gesture is a "peace sign" gesture. In accordance with method 200, the user-performed gesture may then be identified by the processor (130) at act 206 as a "peace sign" gesture; i.e., the gesture in the gesture library that has the largest probability score in the probability vector corresponding to leaf node 320g.

In a second example, the magnitude of the first vector is less than a magnitude of the first value. In this case, the decision tree analysis proceeds along branch 310b to decision node 301c. At decision node 301c, a magnitude of a second feature in the set of features is compared to a magnitude of a second value. In this second example, the magnitude of the second feature is greater than the magnitude of the second value, so the decision tree analysis proceeds along branch 310e to decision node 301e. At decision node 301e, a magnitude of a third feature in the set of features in compared to a magnitude of a third value. In this second example, the magnitude of the third feature is less than the magnitude of the third value, so the decision tree analysis proceeds along branch 310i to leaf node 320c. Leaf node 320c corresponds to a particular probability vector that assigns a particular respective probability score to each gesture in a gesture library. For example, the gesture library may include seven gestures: "finger snap," "thumbs down," etc., and the probability vector of leaf node 320c may assign probability scores to these gestures as (0.7, 0, 0, 0.15, 0.05, 0.1, 0), meaning that the outcome of the decision tree analysis determines that there is a 70% probability that the user-performed gesture is a "finger snap" gesture, a 0% probability that the user-performed gesture is a "thumbs down" gesture, and so on. In accordance with method 200, the user-performed gesture may then be identified by the processor at act 206 as a "finger snap" gesture; i.e., the gesture in the gesture library that has the largest probability score in the probability vector corresponding to leaf node 320c.

Decision tree 300 from FIG. 3 is an illustrative representation of a decision tree. In practice, a decision tree may be embodied or encoded in processor-executable instructions stored in a non-transitory processor-readable storage medium (140). For example, a decision tree, such as decision tree 300, may be encoded in a set of "if then" and/or "if then else" statements written in virtually any computer programming language. In this case, decision node 301a may be embodied by, for example, an "if then else" statement such as:

if |feature $x_1$|>|value A|
    then
    proceed to decision node 301b
    else
    proceed to decision node 301c Similarly, decision node 301b may be embodied by, for example, an "if then else" statement such as:

if |feature $x_2$|>|value B|
    then
    proceed to decision node 301d
    else
    proceed to leaf node 320a And so on. Thus, the logic of a decision tree may be completely encoded in virtually any computer programming language and stored in a non-transitory processor-readable storage memory (140). In some implementations, at least one node may involve comparing the magnitudes of two features rather than comparing the magnitude of one feature to a value. For example, at decision node 301h, a magnitude of a first feature in the set of features may be compared to a magnitude of a second feature in the set of features (i.e., if |feature $x_1$|>|feature $x_2$| then . . . ).

A person of skill in the art will appreciate that a set of "if then else" statements that encodes a decision tree may require very little memory for storage and may be executed very quickly by even a relatively slow, low-power digital processor. Thus, once the structure of a decision tree has been established, processor-executable instructions (141) that encode the decision tree may be stored in a limited non-transitory processor-readable storage medium (140) of a wearable EMG device (100) and readily executed by a relatively slow, low-power on-board digital processor (130). Alternatively, the structure of a decision tree may be hardwired into a circuit such as an ASIC or FPGA and implemented as an on-board processor (130) of a wearable EMG device (100).

As stated above, once the structure of a decision tree has been established, the execution of the decision tree (i.e., performing a decision tree analysis per act 204 of method 200) may be a computationally non-intensive procedure. However, establishing the structure of a decision tree itself can be a very computationally intensive problem. In the art, this process is known as Decision Tree Learning and many techniques have been developed, including but not limited to: Classification And Regression Tree (CART) algorithms, Iterative Dichotomiser 3 (ID3) algorithms, C4.5 algorithms, Chi-squared Automatic Interaction Detector (CHAID) algorithms, and the like. In accordance with the present systems, articles, and methods, virtually any Decision Tree Learning algorithm may be employed to generate a decision tree for use by a processor (130) on-board a wearable EMG device (100) as part of a gesture identification procedure. Likewise, virtually any suitable computing system may be used to execute the Decision Tree Learning algorithm. Since establishing the structure of a decision tree can be a very computationally intensive problem, the Decision Tree Learning algorithm may advantageously be performed using computationally powerful hardware, for example without limitation: at least one computer server, a distributed network of computer systems, multiple processors and/or multiple processor cores, a special-purpose computer system, a quantum computing system, an assembly of graphics processing units, and so on. The Decision Tree Learning algorithm may advantageously employ a large set of "training data" comprising EMG signal data corresponding to multiple trials of each gesture in the gesture library performed by multiple different users. Using such training data, respective features that are characteristic of each respective gesture in the gesture library (i.e., for each gesture in the gesture library, features that are common for that gesture across multiple trials and multiple users) may be identified and used to define decision nodes (301) in the decision tree (300). Defining a decision node (301) may involve, for example, defining which feature(s) in the set of features is/are evaluated and, if applicable, defining the value against which the feature is to be evaluated. For example, in the exemplary "if then else" statement embodiment of decision node 301a provided above, defining decision node 301a involves defining $x_1$ and A. The number of decision nodes 301, the make-up of each decision node 301, the number of branches 310, the layout of branches 310 (i.e., the connectivity between decision nodes 301), the number of leaf nodes 320, and the make-up of each leaf node 320 are all variables in decision tree structure design that may be determined through a Decision Tree Learning procedure. For example, a decision tree may employ non-binary decision nodes, such as decision nodes connected to three or more output branches. It is typically the goal of a Decision Tree Learning procedure to come up with a decision tree structure that uniquely classifies different configurations of the input parameters. Thus, ideally, each leaf node 320 in decision tree 300 would uniquely correspond to a respective gesture in a gesture library such that when a leaf node 320 is reached in a decision tree analysis, a corresponding gesture from the gesture library is returned. However, in practice, such perfect classification may often not be achievable in a single decision tree developed for gesture identification based on EMG signal data from multiple users. The EMG signals produced by different gestures are generally not sufficiently distinct to produce a universally applicable (i.e., across all users) decision tree whose leaf nodes uniquely correspond to respective gestures from a gesture library. In order to accommodate this reality, the decision trees employed in the present systems, articles, and methods, implement leaf nodes 320 that each correspond to a respective probability vector, where each probability vector includes a respective set of probability scores for the gestures in the gesture library.

In some implementations, each leaf node 320 in a decision tree 300 may be encoded as or otherwise represented by a corresponding probability vector. However, in other implementations, it may be advantageous to encode or otherwise represent each leaf node 320 as a respective unique return value (e.g., leaf node 320a=return a; leaf node 320b=return b; etc.). In this case, all of the probability vectors may be stored separately in an array or matrix (e.g., an "Emission matrix" or an "Observation matrix") and a mapping may be performed between return values of the decision tree 300 and probability vectors (e.g., columns or rows) of the Emission matrix. For example, a non-transitory processor-readable storage memory (140) of a wearable EMG device (100) may store a mapping or look-up table and/or processor-executable gesture identification instructions (141) that, when executed by a processor (130), cause the processor (130) to implement the mapping or look-up table or otherwise effect a mapping between return values of the decision tree 300 and probability vectors of the Emission matrix. An advantage of separating the probability vectors (e.g., the Emission matrix) from the decision tree is that such allows either one to be modified without affecting the other.

A decision tree is an example of a classifier that implements a series of evaluations of at least some of the features in the set of features by the processor, wherein each evaluation in the series of evaluations includes evaluating a respective feature in the set of features by the processor, and wherein a first evaluation in the series of evaluations includes evaluating a first feature in the set of features by the processor and each subsequent evaluation in the series of evaluations is based at least in part on an outcome of a previous evaluation in the series of evaluations. In accordance with the present systems, articles, and methods, other forms of classifiers that similarly implement a series of evaluations may substitute for or be used in conjunction with a decision tree. Example classifiers that may be used instead of or in conjunction with a decision tree in accordance with the present systems, articles, and methods include, without limitation: one or more linear classifiers, one or more Bayes classifiers, one or more support vector machines, one or more quadratic classifiers, one or more boosting algorithms, one or more neural networks (e.g., artificial neural networks), one or more Bayesian networks, one or more Hidden Markov Models, and/or the like.

Throughout this specification and the appended claims, the terms "decision tree analysis" and "series of evaluations" are used substantially interchangeably. A person of skill in the art will appreciate, however, that a "decision tree analysis" may, in some cases, be distinct from a "series of evaluations" and/or an application of a "series of evaluations" may be distinct from a "decision tree analysis." For example, in some applications a series of evaluations may be structured in a form other than a decision tree.

A typical user may take on the order of milliseconds to seconds to perform a gesture, and throughout that duration the EMG signals detected and provided at acts 201 and 202, respectively, of method 200 may continuously evolve. If the features determined at act 203 of method 200 are average values, such as respective RMS values of each EMG signal channel, then such features may miss important signal characteristics if they are averaged over the entire duration of the user-performed gesture. In accordance with the present systems, articles, and methods, it can be advantageous to parcel, segment, or otherwise group the time-varying EMG signal from each respective EMG sensor into discrete time windows (synchronized across all of the EMG signals) and to determine at least one respective feature for each time window of each EMG signal. In this way, the resulting features may capture more gesture-specific characteristics that might otherwise be lost in a longer-term averaging process. Furthermore, as the systems, articles, and methods for automated gesture identification described herein are probabilistic, their accuracy may be enhanced by combining the results of multiple analyses across multiple time windows.

As previously described, the set of features may include relationships between features (e.g., ratios, differences, or correlations between features), such as relationships between the respective features of different EMG signals (i.e., signals from different EMG sensors). In applications that include parceling, segmenting, or otherwise grouping the time-varying EMG signal from each respective EMG sensor into discrete time windows, the set of features may include relationships between the respective features of different time windows of the same (or different) EMG signals. In this way, the set of features may characterize how the signal from each EMG sensor (110) changes over time.

Figure 4:
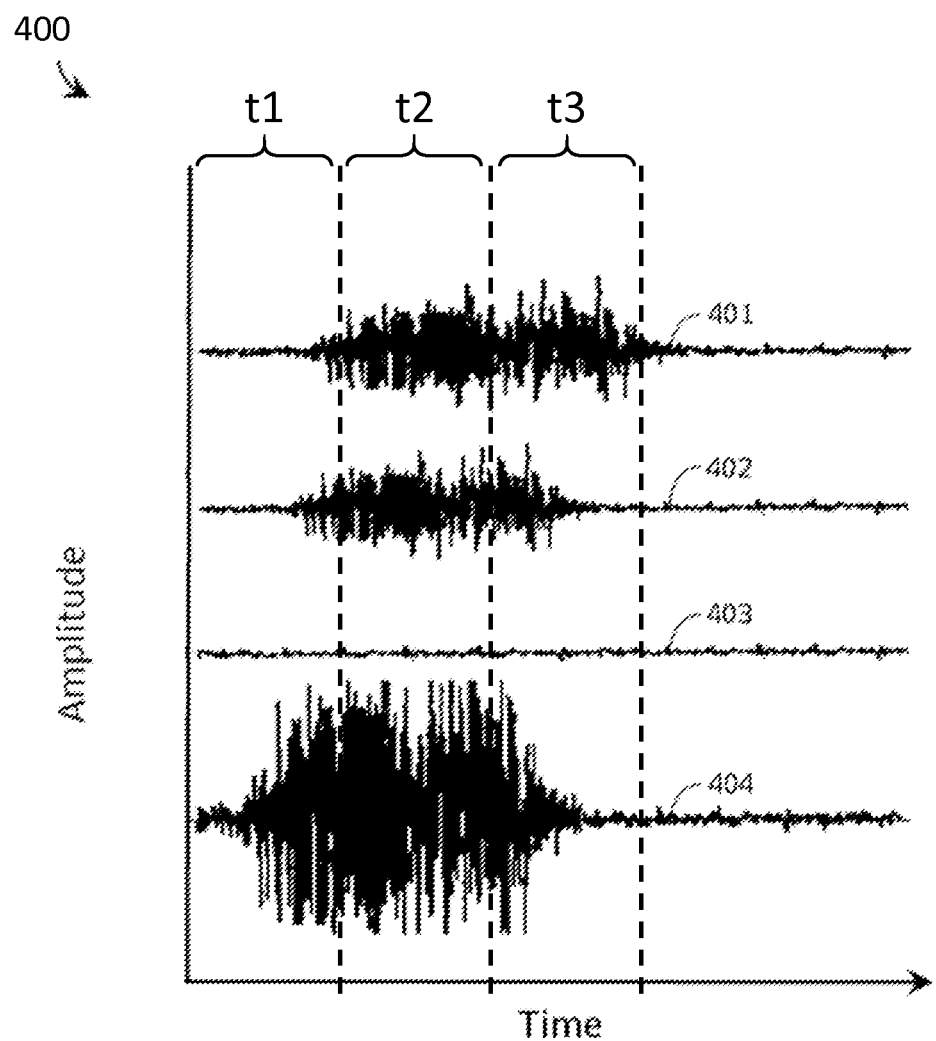
FIG. 4 is a graph showing an exemplary set of four signals corresponding to respective signal channels provided by each of four EMG sensors in a wearable EMG device in accordance with the present systems, articles, and methods.

FIG. 4 is a graph 400 showing an exemplary set of four signals 401, 402, 403, and 404 corresponding to respective signal channels provided by each of four EMG sensors in a wearable EMG device in accordance with the present systems, articles, and methods. For example, signal 401 may represent a signal provided by the EMG sensor 110 of sensor pod 101 in device 100, signal 402 may represent a signal provided by the EMG sensor 110 of sensor pod 103 in device 100, signal 403 may represent a signal provided by the EMG sensor 110 of sensor pod 105 in device 100, and signal 404 may represent a signal provided by the EMG sensor 110 of sensor pod 107 in device 100. Thus, signals 401, 402, 403, 404 may represent a subset of the signals provided by a wearable EMG device having more than four EMG sensors, or they may represent all of the EMG signals provided by a wearable EMG device having four EMG sensors. Each signal 401, 402, 403, and 404 in the set of four signals has a respective amplitude that varies over time.

Each EMG sensor (110) of the wearable EMG device (100) is positioned at a different location on the user (e.g., around the circumference of an armband such as in device 100) and is therefore uniquely positioned relative to various muscles of the user. For example, the EMG sensor (110) that provides signal 403 is positioned relatively close to a first muscle of the user and relatively far from a second muscle of the user, while the EMG sensor (110) that provides signal 404 is positioned relatively far from the first muscle of the user and relatively close to the second muscle of the user. During the time period that is depicted in FIG. 4, the user performs a physical gesture (i.e., a user-performed gesture) that involves substantial activity of some muscles (e.g., substantial activity of the second muscle) and no substantial (or insubstantial) activity of other muscles (e.g., insubstantial activity of the first muscle). Thus, each EMG sensor (110) in the wearable EMG device (100) detects different muscle activity during the gesture and, accordingly, each EMG sensor (110) in the wearable EMG device (100) provides a different signal. As will be described in more detail later, the time period when the user performs the gesture corresponds to the time period when the amplitude of one or more of signals 401, 402, 403, and 404 exceeds some threshold.

Signals 401, 402, 403, and 404 represent EMG signals provided by respective EMG sensors (110) for the duration of a user-performed gesture. The EMG sensors (110) providing signals 401, 402, and 404 detect substantial muscle activity during the user-performed gesture while the EMG sensor (110) providing signal 403 does not detect substantial muscle activity during the user-performed gesture. As per act 203 of method 200 from FIG. 2, the present systems, articles, and methods involve determining a set of features of a set of EMG signals. The set of features may include any or all of various types of signal parameters, characteristics, etc. For example, the set of features may include a respective RMS value of each signal in the set of signals. Thus, as an example, a respective RMS value of each of signals 401, 402, 403, and 404 may be determined at act 203 of method 200. However, as described previously, some features (such as RMS values) can miss important signal characteristics if averaged out over the entire duration of the user-performed gesture. For example, a signal with multiple sharp peaks of high amplitude may produce a long-term RMS feature that is substantially similar to a signal with one broad peak of medium amplitude, even though the two signals clearly represent different muscle activity. In accordance with the present systems, articles, and methods, it can be advantageous to parcel, segment, or otherwise group the time-varying EMG signal from each respective EMG sensor (110) into discrete time windows (time-synchronized across the signals from all EMG sensors) and to determine at least one respective feature for each time window of each EMG signal. In FIG. 4, each of signals 401, 402, 403, and 404 is divided into three time-synchronized time windows: t1, t2, and t3. Three time windows are used in FIG. 4 for illustrative purposes only. In alternative embodiments or applications, any number and/or size of time window(s) may be employed. Furthermore, time windows t1, t2, and t3 in FIG. 4 are serially-connected, whereas in alternative embodiments any or all time windows may overlap or there may be gaps therebetween.

Throughout this specification and the appended claims, the term "time-synchronized" as in "time-synchronized time windows" is used to indicate that the time windows for each respective EMG signal (e.g., each of EMG signals 401, 402, 403, and 404) are substantially synchronized in time across all of the EMG signals. In other words, a first time-synchronized time window t1 represents substantially the same first window of time for each EMG signal in a set of EMG signals (e.g., for each of signals 401, 402, 403, and 404), a second time-synchronized time window t2 represents substantially the same second window of time for each EMG signal in the set of EMG signals (e.g., for each of signals 401, 402, 403, and 404), and so on.

In accordance with the present systems, articles, and methods, at least one respective feature of each EMG signal may be determined for each respective time-synchronized time window. For example, a set of features determined per act 203 of method 200 may include a set of features that are all determined for the same time window, such as a first feature determined for signal 401 in time window t1, a second feature for signal 402 in time window t1, a third feature determined for signal 403 in time window t1, and a fourth feature determined for signal 404 in time window t1. The set of features all determined for the same time window (e.g., the set of features of signals 401, 402, 403, and 404 all determined for time window t1) may then be processed per, for example, acts 204 and 205 of method 200. An outcome of act 205 of method 200, using a set of features all corresponding to the same time window, is a probability vector including a respective probability score of each gesture in a gesture library. In accordance with the present systems, articles, and methods, the probability scores determined for the gestures in a gesture library based on a first time window of EMG signal data may be combined with the probability scores determined for the gestures in the same gesture library based on at least a second time window of the same EMG signal data. Combining the outcomes of multiple decision tree analyses (each performed for features corresponding to a respective time window) can augment the accuracy and reliability of the probabilistic gesture identification procedure exemplified, for example, by method 200 in FIG. 2. Acts 203, 204, and 205 of method 200 may be carried out multiple times (e.g., iteratively) for various parcels, segments, sections, etc. (i.e., time windows) of the signals from acts 201 and 202. The respective results of multiple iterations, rounds, or instances of acts 203, 204, and 205 may be combined in order to identify the user-performed gesture per act 206.

In some applications, acts 201 and 202 of method 200 may be carried out for a relatively large period of time (i.e., a length of time that exceeds the duration of a user-performed gesture) with at least a portion of the corresponding data being stored in a non-transitory processor-readable medium (140). The data may then be parceled, segmented, divided, or otherwise grouped into time windows as described above and respective iterations, rounds, or instances of acts 203, 204, and 205 may be carried out for each respective time window. Thus, data may be collected throughout a user-performed gesture, stored, and subsequently processed by parceling, segmenting, dividing, or otherwise grouping the data into time windows. However, this approach disadvantageously requires that all of the EMG signal data corresponding to a user-performed gesture be collected per acts 201 and 202 before the data analysis of acts 203, 204, and 205 is carried out to produce an automated gesture identification per act 206. Such is not particularly well-suited to real-time gesture identification. In other applications, it can be advantageous to continuously collect EMG signal data per acts 201 and 202 and to actively capture the EMG signal data into time windows and perform acts 203, 204, and 205 substantially in real-time. For example, acts 201 and 202 may be performed continuously, or substantially continuously, beginning at time t0. After EMG signal data has been captured for the duration of a first time window t1, acts 203, 204, and 205 may be performed using the EMG signal data captured during the first time window t1. While acts 203, 204, and 205 are being performed for the first time window t1, acts 201 and 202 may continue to be carried out for a second time window t2. After EMG signal data has been captured for the duration of the second time window t2, acts 203, 204, and 205 may be performed using the EMG signal data captured during the second time window t2 (i.e., EMG signal data collected while acts 203, 204, and 205 were being performed using the EMG signal data collected during the first time window t1). While acts 203, 204, and 205 are being performed for the second time window t2, acts 201 and 202 may continue to be carried out for a third time window t3, and so on.

Figure 5:
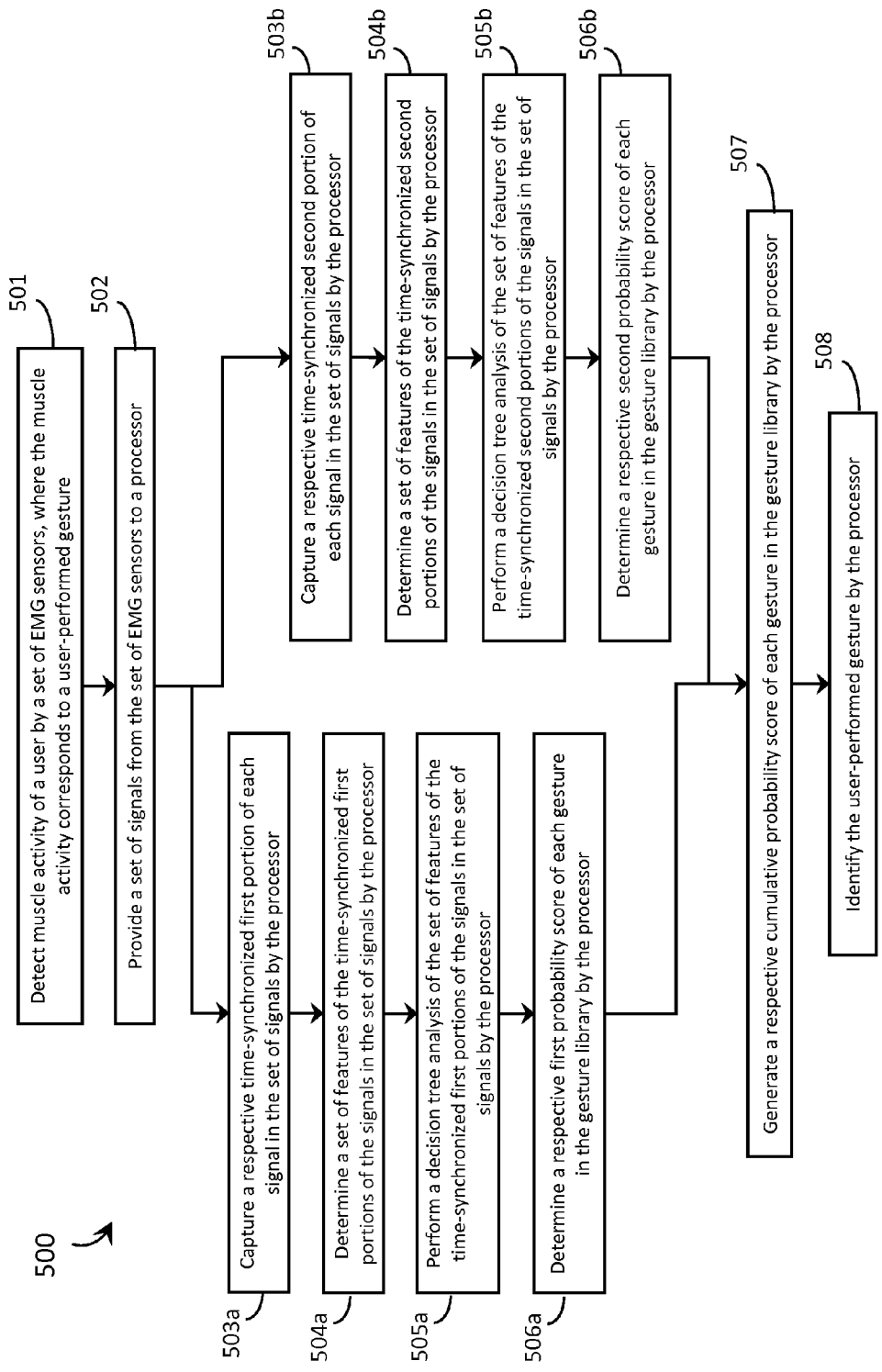
FIG. 5 is a flow-diagram showing a method of operating a wearable EMG device in accordance with the present systems, articles, and methods.

FIG. 5 is a flow-diagram showing a method 500 of operating a wearable EMG device in accordance with the present systems, articles, and methods. Method 500 is similar to method 200 from FIG. 2 in that method 500 is a method of identifying a gesture performed (e.g., identifying which gesture in a gesture library is performed) by a user of a wearable EMG device. The wearable EMG device includes a set of EMG sensors (the set of EMG sensors including multiple EMG sensors, i.e., at least two EMG sensors) and a processor and may form part of a human-electronics interface in which the wearable EMG device is used to provide gesture-based interaction with an electronic device.

Method 500 includes eight acts 501, 502, 503, 504, 505, 506, 507, and 508, where at least two iterations, rounds, or instances of acts 503, 504, 505, and 506 are performed in between acts 502 and 507. The at least two iterations, rounds, or instances of acts 503, 504, 505, and 506 are labeled as 503a/b, 504a/b, 505a/b, and 506a/b, respectively. Those of skill in the art will appreciate that in alternative embodiments certain acts may be omitted and/or additional acts may be added. Those of skill in the art will also appreciate that the illustrated order of the acts is shown for exemplary purposes only and may change in alternative embodiments. For the purpose of method 500, the term "user" refers to a person that is wearing the wearable EMG device.

Acts 501 and 502 of method 500 are substantially similar to acts 201 and 202, respectively, of method 200.

At 501, a set of EMG sensors (110) detects muscle activity of a user of the wearable EMG device (100). The muscle activity corresponds to a user-performed gesture (i.e., a physical gesture that is performed by the user). As an example, the wearable EMG device (100) may be worn on an arm of the user and the physical gesture may include a hand gesture such as a finger curl, a splaying gesture, a finger flick, etc.

At 502, the set of EMG sensors (110) provides a set of signals to the processor (130) of the wearable EMG device (100) in response to the detected muscle activity of act 501. The signals may be, for example, electrical or optical signals routed from the EMG sensors (110) to the processor (130) through electrically conductive or optical communicative pathways (121, 122). Providing a set of signals from the set of EMG sensors (110) to the processor (130) may include providing a respective signal from each respective EMG sensor (110) in the set of EMG sensors to the processor (130). For example, each EMG sensor (110) in the set of EMG sensors may communicatively couple to the processor (130) using a respective signal channel to provide either analog or digital signals to the processor (130).

As described previously, the acts of detecting muscle activity of a user and providing EMG signals in response to the detected muscle activity (i.e., acts 501 and 502, respectively) may be carried out substantially continuously by a wearable EMG device (100). An activation threshold may be defined, and when the user performs a physical gesture one or more of the signals provided by the EMG sensors (e.g., the amplitude/magnitude of one or more of the signals) per act 502 may exceed the activation threshold. The time at which the activation threshold is exceed may trigger the beginning (i.e., initialization) of a first time window.

At 503a, the processor (130) of the wearable EMG device (100) captures a respective time-synchronized first portion (i.e., a first time window) of each signal in the set of signals (i.e., each signal provided by a respective EMG sensor (110) at act 502). As described previously, the respective time-synchronized first portion of each signal in the set of signals may be a respective parcel, segment, section, or window of the substantially continuous data stream provided by the EMG sensors (110) per act 502. The time-synchronized first portion of each signal in the set of signals may correspond to a first time window t1, as illustrated in FIG. 4.

Acts 504a, 505a, and 506a of method 500 are substantially similar to acts 203, 204, and 205, respectively, of method 200 except that acts 504a, 505a, and 506a are each specifically performed or carried out on/using the time-synchronized first portions of the signals in the set of signals.

At 504a, the processor (130) of the wearable EMG device (100) determines a set of features of the time-synchronized first portions of the signals in the set of signals. The set of features may include characteristics, parameters, magnitudes, or generally any property or properties of the time-synchronized first portions of the signals in the set of signals. Determining the set of features of the time-synchronized first portions of the signals in the set of signals by the processor (130) may include determining a respective feature or respective features of the respective time-synchronized first portion of each signal in the set of signals by the processor (130).

At 505a, the processor (130) of the wearable EMG device (100) performs a decision tree analysis of the set of features of the time-synchronized first portions of the signals in the set of signals. The decision tree analysis may include, for example, performing a series of evaluations of at least some of the features in the set of features by the processor (130), as described for the illustrative example of decision tree 300 in FIG. 3.

At 506a, the processor (130) determines a respective probability score of each gesture in the gesture library based at least in part on an outcome of the decision tree analysis. For example, the outcome of the decision tree analysis may be a probability vector comprising a set of numbers that each represents the probability that the user-performed gesture is a respective gesture from the gesture library.

As described previously, a time-synchronized second portion (i.e., a second time window) of each signal in the set of signals may be captured and processed in series, in parallel, in tandem, or otherwise in combination with the time-synchronized first portion (i.e., the first time window) of each signal in the set of signals. For example, in method 500, acts 503a, 504a, 505a, and 506a represent the capturing and processing of a time-synchronized first portion of each signal in the set of signals and acts 503b, 504b, 505b, and 506b represent the capturing and processing of a time-synchronized second portion of each signal in the set of signals. Acts 503b, 504b, 505b, and 506b are substantially similar to acts 503a, 504a, 505a, and 506a (respectively) except that acts 503b, 504b, 505b, and 506b are performed or carried out on/using time-synchronized second portions of the signals provided by the EMG sensors (110) while acts 503a, 504a, 505a, and 506a are performed or carried out on/using time synchronized first portions of the signals provided by the EMG sensors (110). In FIG. 5, acts 503b, 504b, 505b, and 506b are shown vertically offset from (i.e., shifted downwards with respect to) acts 503a, 504a, 505a, and 506a to represent that the time-synchronized second portions of the signals in the set of signals correspond to a time window that begins after the beginning of the time-synchronized first portions of the signals in the set of signals and extends after the end of the time-synchronized first portions of the signals in the set of signals.

At 503b, the processor (130) of the wearable EMG device (100) captures a respective time-synchronized second portion of each signal in the set of signals (i.e., each signal provided by a respective EMG sensor (110) at act 502). As described previously, the respective time-synchronized second portion of each signal in the set of signals may be a respective parcel, segment, section, or window of the substantially continuous data stream provided by the EMG sensors (110) per act 502. The time-synchronized second portion of each signal in the set of signals may correspond to a second time window t2, as illustrated in FIG. 4. The time-synchronized second portion of each signal in the set of signals (e.g., the second time window t2 illustrated in FIG. 4) may begin at least approximately when the time-synchronized first portion of each signal in the set of signals (e.g., the first time window t1 illustrated in FIG. 4) ends as illustrated in FIG. 4, or the time-synchronized second portion of each signal in the set of signals may overlap with (and extend beyond the end of) the time-synchronized first portion of each signal in the set of signals, or there may be a gap between the end of the time-synchronized first portion of each signal in the set of signals and the beginning of the time-synchronized second portion of each signal in the set of signals.

At 504b, the processor (130) of the wearable EMG device (100) determines a set of features of the time-synchronized second portions of the signals in the set of signals in substantially the same way as described for act 504a and act 203 of method 200.

At 505b, the processor (130) of the wearable EMG device (100) performs a decision tree analysis of the set of features of the time-synchronized second portions of the signals in the set of signals in substantially the same way as described for act 505a and act 204 of method 200.

At 506b, the processor (130) determines a respective probability score of each gesture in the gesture library based at least in part on an outcome of the decision tree analysis in substantially the same way as described for act 506a and act 205 of method 200.

As illustrated in FIG. 5, method 500 includes two iterations, rounds, or instances of acts 503, 504, 505, and 506 (i.e., 503a/b, 504a/b, 505a/b, and 506a/b, respectively) corresponding to two time-synchronized portions of each signal in the set of signals (e.g., two time windows). However, in practice, method 500 may include any number of iterations, rounds, or instances of acts 503, 504, 505, and 506 corresponding to any number of time-synchronized portions of each signal in the set of signals (e.g., any number of time windows), including more than two iterations, rounds, or instances of acts 503, 504, 505, and 506.

At 507, the processor (130) combines the results of the multiple iterations, rounds, or instances of acts 503, 504, 505, and 506 (e.g., the results of acts 503a/b, 504a/b, 505a/b, and 506a/b) to generate a respective cumulative probability score of each gesture in the gesture library. For example, the respective cumulative probability score of each gesture in the gesture library may be based, at least in part, on both the respective first probability score of each gesture in the gesture library determined at act 506a and the respective second probability score of each gesture in the gesture library determined at 506b. The probability vectors determined at the multiple iterations, rounds, or instances of act 506 may be combined in a variety of different ways depending on the specific implementation. Generating a cumulative probability score of any particular gesture in the gesture library may include multiplying, averaging, or otherwise combining the respective probability scores for the particular gesture determined at each respective iteration, round, or instance of act 506. For example, generating a cumulative probability score of Gesture A in the gesture library at act 507 may include multiplying, averaging, or otherwise combining (by the processor (130)) the first probability score for Gesture A determined at act 506a and the second probability score for Gesture A determined at act 506b. In some applications, combining multiple probability scores may involve applying a weighting or scalar multiplier to one or more probability score(s) based on, for example, the time window to which the probability score corresponds.

At 508, the processor (130) of the wearable EMG device (100) identifies the user-performed gesture based at least in part on the cumulative probability score of at least one gesture in the gesture library generated at act 507. For example, the gesture in the gesture library that has the largest cumulative probability score as determined at act 507 may be identified by the processor (130) at act 508 as the user-performed gesture.

As will be clear to a person of skill in the art based on the description of FIG. 5, the various embodiments described herein include iterative methods for performing automated gesture identification in real-time. Each iteration in such an iterative method may correspond to a respective time-synchronized portion or window of the data streams provided by the EMG sensors (110) of a wearable EMG device (100). This concept is illustrated in FIG. 6.

Figure 6:
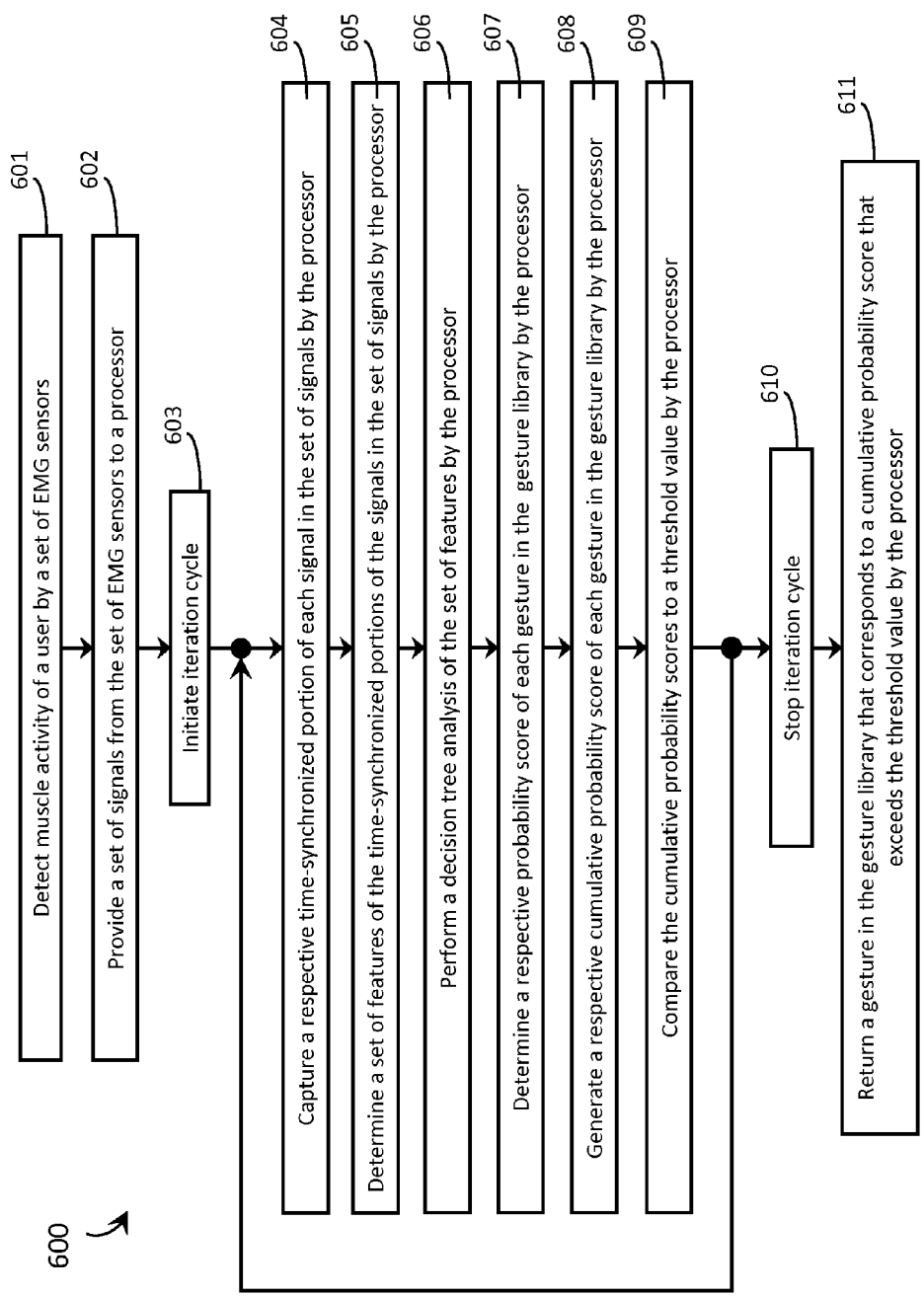
FIG. 6 is a flow-diagram showing a method of identifying which gesture in a gesture library is performed by a user of a wearable EMG device in accordance with the present systems, articles, and methods.

FIG. 6 is a flow-diagram showing a method 600 of identifying which gesture in a gesture library is performed by a user of a wearable EMG device in accordance with the present systems, articles, and methods. The wearable EMG device includes a set of EMG sensors (the set of EMG sensors including multiple EMG sensors, i.e., at least two EMG sensors) and a processor communicatively coupled to the set of EMG sensors, and may form part of a human-electronics interface in which the wearable EMG device is used to provide gesture-based interaction with and/or control of an electronic device.

Method 600 includes eleven acts 601, 602, 603, 604, 605, 606, 607, 608, 609, 610, and 611, though those of skill in the art will appreciate that in alternative embodiments certain acts may be omitted and/or additional acts may be added. Those of skill in the art will also appreciate that the illustrated order of the acts is shown for exemplary purposes only and may change in alternative embodiments. Method 600 is an iterative method in which acts 604-609 may be performed any number of times. For the purpose of method 600, the term "user" refers to a person that is wearing the wearable EMG device.

At 601, the set of EMG sensors (110) detects muscle activity of a user in response to the user performing a physical gesture. Act 601 may be substantially similar to act 201 from method 200 and act 501 from method 500.

At 602, the set of EMG sensors (110) provides a set of signals to the processor (130) of the wearable EMG device (100) in response to the detected muscle activity from act 601. Each signal in the set of signals may be provided by a respective one of the EMG sensors (110) in the set of EMG sensors. Act 602 may be substantially similar to act 202 from method 200 and act 502 from method 500.

Depending on the nature of the EMG sensors employed, acts 601 and 602 may be performed or carried out substantially continuously by the wearable EMG device (100), either at all times (while the device is worn by the user) or specifically whenever the user performs a gesture involving sufficient muscle activity so as to be detected by the EMG sensors (110) per act 601. For example, a capacitive EMG sensor that is capacitively coupled to electrical activity in a user's arm may substantially continuously detect (per act 601) any detectable changes in that electrical activity and may substantially continuously provide (per act 602) signals in response to any detectable changes. In this case, the acts of detecting muscle activity (601) and providing signals (602) may be performed substantially concurrently, or sequentially with a substantially negligible delay to account for signal propagation. In order to help distinguish the muscle activity of a deliberate gesture from background muscle activity (such as the muscle activity produced when a user is simply walking or scratching their head), the wearable EMG device (100) may be configured to implement one or more activation thresholds. For example, acts 603-611 involve or are based on processing the signals provided by the EMG sensors (110) at act 602. In applications that employ one or more activation thresholds, acts 603-611 of method 600 may only be performed or carried out when at least one signal provided by at least one EMG sensor (110) at act 602 exceeds an activation threshold (e.g., as determined by the processor (130)).

At 603, an iteration cycle is initiated. Each iteration involves performing acts 604, 605, 606, 607, 608, and 609, and the iteration cycle is repeated until a cumulative probability score that exceeds a threshold value is identified.

At 604, the processor (130) of the wearable EMG device (100) captures a respective time-synchronized portion (i.e., a respective time-synchronized time window) of each signal in the set of signals provided by the EMG sensors (110) at act 602. For example, in a first iteration a respective time-synchronized first portion (or first time window) of each signal is captured, in a second iteration a respective time-synchronized second portion (or second time window) of each signal is captured, and so on, up to a final $N^{th}$ iteration in which a respective time-synchronized $N^{th}$ portion (or $N^{th}$ time window) of each signal is captured (where N is an integer equal to the number of iterations performed). As described previously, the respective time-synchronized portions of successive iterations may be serially/sequentially connected, or they may overlap, or there may be gaps therebetween. Capturing a respective time-synchronized portion of each signal in the set of signals may include, for example, collecting and storing data from each signal in the set of signals for a defined period of time, such as from a beginning point $t_{start}$ to an end point $t_{end}$.

At 605, the processor (130) determines a set of features of the time-synchronized portions of the signals in the set of signals. As described previously (e.g., in the context of act 203 of method 200 and act 504 of method 500), the set of features may include any characteristics, parameters, or aspects of the set of signals (such as RMS values) and/or relationships between signals such as differences, ratios, and/or correlations.

At 606, the processor (130) performs a decision tree analysis of the set of features. The decision tree analysis may employ a decision tree such as decision tree 300 from FIG. 3 (or, more generally, any type of classifier) that lends structure to a series of evaluations of at least some of the features in the set of features.

At 607, the processor (130) determines a respective probability score of each gesture in the gesture library, based at least in part on an outcome of the decision tree analysis from act 606. The probability scores may be contained in or otherwise represented by a probability vector, where each respective element of the probability vector corresponds to the probability score of a respective gesture in the gesture library. In some implementations, a set of probability vectors may be incorporated into the decision tree structure used for the decision tree analysis of act 606, where each respective probability vector in the set of probability vectors corresponds to a respective leaf node of the decision tree (as in, for example, leaf nodes 320a-320j of decision tree 300 in FIG. 3). In this case, determining a respective probability score of each gesture in the gesture library per act 607 may essentially be an outcome of (e.g., the final act of) performing a decision tree analysis on the set of features per act 606. Performing a decision tree analysis on the set of features may essentially map (or more generally, effect a mapping from) the set of features to a probability vector.

At 608, the processor (130) generates a respective cumulative probability score of each gesture in the gesture library. In a similar way to that described for act 507 of method 500, the cumulative probability score of a gesture in the gesture library is a combination of the probability score determined for the gesture at act 607 of the current iteration with the probability score(s) determined for the same gesture at act 607 of any or all previous iteration(s). In a first iteration of the iteration cycle initiated at act 603, the respective cumulative probability score of each gesture in the gesture library generated at act 608 may be equal to the respective probability score of each gesture in the gesture library determined at act 607. In a second iteration of the iteration cycle initiated at act 603, the respective cumulative probability score of each gesture in the gesture library generated at act 608 may be based on combining the respective first probability score of each gesture in the gesture library determined at act 607 of the first iteration with the respective second probability score of each gesture in the gesture library determined at act 607 of the second iteration. In a third iteration of the iteration cycle initiated at act 603, the respective cumulative probability score of each gesture in the gesture library generated at act 608 may be based on combining the respective first probability score of each gesture in the gesture library determined at act 607 of the first iteration with the respective second probability score of each gesture in the gesture library determined at act 607 of the second iteration and with the respective third probability score of each gesture in the gesture library determined at act 607 of the third iteration; and so on up the $N^{th}$ (i.e., final) iteration. In some implementations, generating a respective cumulative probability score of each gesture in the gesture library in an $i^{th}$ iteration may simply involve combining the respective probability score of each gesture in the gesture library determined at act 607 of the $i^{th}$ iteration with the respective cumulative probability score of each gesture in the gesture library determined at act 608 of the $(i-1)^{th}$ (i.e., the previous) iteration. Generating a cumulative probability score of a gesture may involve multiplying, averaging, or otherwise combining the respective probability scores of the gesture from multiple iterations.

At 609, the processor (130) compares the cumulative probability scores to a threshold value. The threshold value may include, for example, a minimum acceptable cumulative probability score or a value that somehow relates a cumulative probability score and a number of iterations (e.g., a minimum cumulative probability score given the number of iterations, a minimum cumulative probability score after a certain number of iterations, etc.). In some implementations, the number of iterations may be monitored directly and similarly compared to a threshold, such as a minimum number of iterations, a maximum number of iterations, etc. The threshold value may be stored in a non-transitory processor-readable storage medium (140) of the wearable EMG device (100). If none of the cumulative probability scores generated at act 608 meet or exceed the threshold value in the comparison at act 609, then the current iteration completes and method 600 returns to act 604 to begin another iteration. In this case, either the respective probability score of each gesture in the gesture library determined at act 607 of the iteration, or the cumulative probability score of each gesture in the gesture library determined at act 608 of the iteration, or both, may be stored in the non-transitory processor-readable storage medium (140) of the wearable EMG device (100) for subsequent use in generating a respective cumulative probability score of each gesture in the gesture library at act 609 of the next iteration. If one or more of the cumulative probability scores generated at act 608 meet or exceed the threshold value in the comparison of act 609, then method 600 proceeds to act 610. Likewise, in some implementations, if the number of iterations exceeds a corresponding threshold, method 600 may proceed to act 610.

At 610, the iteration cycle is stopped. In accordance with the present systems, articles, and methods, "stopping" the iteration cycle per act 610 is generally referenced as a trigger for act 611. In some implementations, act 610 may be omitted such that act 611 is executed directly after an instance of act 609 without stopping the iteration cycle of acts 604-609. In other words, some implementations of method 600 may continue to perform acts 601, 602, and 604-609 essentially indefinitely (i.e., while the wearable EMG device (100) is powered on and active) and only extend to include act 611 in iterations where one or more of the cumulative probability scores generated at act 608 meet or exceed the threshold value in the comparison of act 609.

At 611, the processor (130) returns a gesture in the gesture library that corresponds to a cumulative probability score that meets or exceeds the threshold value. If the cumulative probability score of more than one gesture in the gesture library is found to meet or exceed the threshold value in the comparison of act 609, then the gesture in the gesture library that corresponds to the largest cumulative probability score may be returned at act 611.

Method 600 may be implemented, executed, performed, or otherwise carried out by exemplary wearable EMG device 100 from FIG. 1, or more generally by any wearable EMG device that includes: a set of EMG sensors (110) responsive to (i.e., to detect) muscle activity corresponding to a gesture performed by a user of the wearable EMG device (100) per act 601 and that provides a set of signals in response to the detected muscle activity per 602; a processor (130) communicatively coupled to the set of EMG sensors (110); and a non-transitory processor-readable storage medium (140) communicatively coupled to the processor (130). The non-transitory processor-readable storage medium (140) may store processor-executable gesture identification instructions (141) that, when executed by the processor (130), cause the processor (130) to: i) until a cumulative probability score that exceeds a threshold value is identified, iteratively (per act 603): capture a respective time-synchronized portion of each signal in the set of signals per act 604; determine a set of features of the time-synchronized portions of the signals per act 605; perform a decision tree analysis of the set of features per act 606; determine a respective probability score of each gesture in the gesture library per act 607; generate a respective cumulative probability score of each gesture in the gesture library per act 608, where the cumulative probability score of each respective gesture in the gesture library combines the probability score of the gesture in the current iteration with any and all probability scores of the gesture from any and all previous iterations; and compare the cumulative probability scores in the set of cumulative probability scores to the threshold value per act 609; and ii) in response to identifying a cumulative probability score that exceeds a threshold value: stop the iteration per act 610; and return the gesture in the gesture library that corresponds to the cumulative probability score that exceeds the threshold value per act 611.

The signals that are detected and provided by the EMG sensors (110) of a wearable EMG device (100) when a user performs a gesture may not be identical each time the same gesture is performed. Discrepancies between different instances of the same gesture may result from variations in many different use parameters, including but not limited to: signal noise, discrepancies in how the gesture is performed, shifts or variations in the orientation and/or position of the wearable EMG device (100) during or between gestures, a different user performing the same gesture, muscle fatigue, a change in environmental or skin conditions, etc. The various embodiments described herein provide systems, articles, and methods for operating a wearable EMG device (100) to identify a gesture (or gestures) performed by a user with improved robustness against such variations in use parameters. Improved robustness is achieved, at least in part, by determining and applying a generalized decision tree or classifier (such as decision tree 300 in FIG. 3) based on a set of training data (e.g., a large set of training data, such as EMG signal data for tens, hundreds, thousands, or more users each performing multiple instances of multiple gestures) that effects a mapping from features of the signals provided by the EMG sensors (110) to probability scores for gestures in a gesture library. Furthermore, the generalized decision tree or classifier is a relatively small (in terms of system memory required for storage) piece of software that can readily be executed by a relatively low-power, low-performance processor.

As previously described, in some applications it may be advantageous to combine EMG signals with motion signals sensed, measured, or otherwise detected by, for example, at least one inertial sensor such as a linear accelerometer and/or a gyroscope. To this end, any or all of the systems, articles, and methods for wearable EMG devices (100) described herein may include at least one inertial sensor (e.g., IMU 160 of device 100) responsive to motion, and any or all of methods 200, 500, and/or 600 may further include detecting motion corresponding to the gesture performed by the user by the at least one inertial sensor (160), providing at least one signal from the at least one inertial sensor (160) to the processor (130) of the wearable EMG device (100) in response to the detected motion, and processing the at least one signal from the at least one inertial sensor (160) by the processor (130). In this case, identifying the user-performed gesture by the processor (130) based at least in part on the (cumulative) probability score of at least one gesture in the gesture library may include identifying the user-performed gesture by the processor (130) based at least in part on an outcome of the processing the at least one signal from the at least one inertial sensor (160) by the processor (130). For example, identifying the user-performed gesture by the processor (130) may include combining the at least one signal from the at least one inertial sensor (160) at or with any stage of the processing of the set of signals from the EMG sensors (110), such as combining the at least one signal from the at least one inertial sensor (160) with the set of signals from the EMG sensors (110), and/or combining the at least one signal from the at least one inertial sensor (160) with the probability scores of the gestures in the gesture library, etc. The inclusion of motion-based signal data can significantly increase the number of gestures that can be identified by the wearable EMG device (100) and/or increase the distinctiveness of each gesture. For example, a "finger snap" gesture may, in some implementations, be difficult to discern using a decision tree analysis applied to EMG signal data alone, but accurate identification of a "finger snap" gesture may be significantly augmented by combining the EMG signal data with inertial and/or motion data provided by at least one inertial and/or motion sensor (160).

The ability of the wearable EMG devices described herein to accurately identify gestures may benefit, in some implementations, from specific information about at least some use parameters. For example, in order for a wearable EMG device (100) to perform accurate gesture identification as described herein, the wearable EMG device (100) may require information about the location, position, and/or orientation of its EMG sensors (110) in relation to the muscles of the user. In accordance with the present systems, articles, and methods, all of the necessary information about the location, position, and/or orientation of the EMG sensors (110) may be readily collected by the wearable EMG device (100) by having the user perform a single reference gesture when the wearable EMG device (100) is first donned. Such is a considerable improvement over the elaborate training procedures (requiring the user to perform a series of multiple trials for each of multiple gestures) required by known proposals for wearable EMG devices that perform gesture identification.

A user may be instructed to don a wearable EMG device on, for example, one of their forearms with any orientation and at any location above the wrist and below the elbow that provides a comfortable, snug fit. A feature of exemplary wearable EMG device 100 from FIG. 1 is that the order of the EMG sensors 110 around the perimeter of the device 100 is fixed. That is, each EMG sensor 110 is positioned adjacent and in between the same two other EMG sensors 110 regardless of the position and/or orientation of the device 100. Furthermore, the angular spacing between EMG sensors 110 remains substantially constant as described in U.S. Provisional Patent Application Ser. No. 61/860,063 (now U.S. Non-Provisional patent application Ser. No. 14/276,575), which is incorporated herein by reference in its entirety. Thus, assuming the device 100 is snugly fit on the forearm of the user, in order to determine the position and/or orientation of the EMG sensors 110 on the forearm of the user, only three things need to be determined by the wearable EMG device 100: i) on which arm of the user is the device 100 being worn, ii) what is the rotational orientation of the device 100; and iii) what is the front-to-back orientation of the device 100? In accordance with the present systems, articles, and methods, having the user perform a single reference gesture can provide all of the information necessary to answer each of these three questions. An example of answering each of these three questions (i.e., determining position and orientation information of the wearable EMG device) using a single reference gesture is now described. For the example that follows, the device 100 includes an IMU 160 (such as an MPU-9150 Nine-Axis MEMS MotionTracking™ Device from InvenSense) that includes multi-axis accelerometers, gyroscopes, and a compass, and the reference gesture is: begin with the arm (i.e., the arm upon which the device is worn) extended out in front and with the hand forming a loose first with the thumb on top such that the back or dorsal side of the thumb faces upwards, then open the hand and bend the wrist outwards such that the open palm faces forwards and the extended fingers point outwards approaching ninety degrees to the forearm (i.e., as far past about forty-five degrees that is comfortable for the user). A person of skill in the art will appreciate that the combination of IMU and reference gesture data used in this example is not limiting and that many alternative reference gestures and/or motion-detecting devices may similarly be used.

i) On which arm of the user is device 100 being worn?

The reference gesture used in this example causes a small change in the yaw of the wearable EMG device 100. As the user's wrist bends back outwardly, the user's forearm shifts slightly inward. This change in the yaw is determined from signals provided by the IMU 160 and indicates on which arm of the user the device 100 is being worn. For example, a negative change in yaw from the sensor's perspective may indicate that the device 100 is worn on the right arm of the user while a positive change in the yaw may indicate that the device 100 is worn on the left arm of the user. Yaw calculation from accelerometer, gyroscope, and/or compass data can employ any number of techniques including without limitation: sensor fusion algorithms, quaternion-based methods, and the like.

ii) What is the rotational orientation of device 100?

The rotational orientation of device 100 influences which EMG sensors 110 overlie and/or are most proximate to which specific muscle groups in the user's forearm. While device 100 is worn on a forearm of the user, the rotational orientation may be changed by: a) holding device 100 fixed in space with the user's other hand and rotating, twisting, or pronating the forearm upon which the device 100 is worn about the longitudinal axis of the forearm (e.g., from a palm facing up position to a palm facing down position), or b) holding the forearm upon which the device 100 is worn fixed in space and using the other hand to spin the device 100 about the longitudinal axis of the fixed forearm. Returning to the example of FIG. 4, the rotational orientation of device 100 determines which EMG sensor 110 overlies which muscles of the forearm and so determines which EMG sensors provides which signal 401, 402, 403, or 404. In a first rotational orientation, the EMG sensor 110 of sensor pod 101 may provide signal 401, the EMG sensor 110 of sensor pod 103 may provide signal 402, and so on, but in a different rotational orientation, the EMG sensor 110 of sensor pod 106 may provide signal 401, the EMG sensor 110 of sensor pod 108 may provide signal 402, and so on. Neither of these orientations is "more correct" than the other. When the user performs the reference gesture, two adjacent EMG sensors 110 of device 100 detect coincident spikes in muscle activity corresponding to activation of the muscles on the outside or posterior side of the user's arm (e.g., the extensor digitorum, the extensor digiti minimi, and/or the extensor carpi ulnaris). Thus, the rotational orientation of device 100 is determined to be either one of two rotational orientations that place the two spiking EMG sensors 110 proximate the active muscles. The two rotational orientations are distinguished by the front-to-back orientation of device 100 (i.e., the two rotational orientations are front-to-back variants of one another).

iii) What is the front-to-back orientation of device 100?

The front-to-back orientation of device 100 is established by the side through which the user's hand enters the opening of the closed loop configuration of device 100. For example, in a first front-to-back orientation tethered connector-port 152 of device 100 faces proximally towards the user's elbow and in a second front-to-back orientation tethered connector port 152 faces distally towards the user's hand. When the user performs the reference gesture, the front-to-back orientation of device 100 is determined by the absolute roll of device 100, which is detected by IMU 160. Roll calculation from accelerometer, gyroscope, and/or compass data may employ any of a variety of techniques including without limitation: sensor fusion algorithms, quaternion-based methods, and the like.

As described for the exemplary reference gesture above, a user may calibrate a wearable EMG device in accordance with the present systems, articles, and methods by performing only a single reference gesture. No further training procedures may be required before the device can begin identifying gestures performed by the user.

Any given gesture may produce a specific pattern of muscle activity detected by the EMG sensors (110), but how the detected muscle activity is distributed among the EMG sensors (i.e., which EMG sensor(s) detect which muscle activity) depends on the position and/or orientation of the EMG sensors (110) on the user's arm. Information about the position and/or orientation of the EMG sensors (110) that is collected by the wearable EMG device (100) when the user performs the reference gesture may be used, for example, to calibrate the decision tree, classifier, or series of evaluations that is/are applied to the set of features of the EMG signal data during the gesture identification procedures described herein. For example, information about the position and/or orientation of the EMG sensors (110) may be used to influence or determine which feature in the set of features is evaluated (e.g., compared to a value) at each decision node 301 in a decision tree 300 and/or the magnitude of the value to which the feature is compared.

In accordance with the present systems, articles, and methods, changes in the position and/or orientation of the wearable EMG device (100) may produce changes (e.g., shifts, rotations, etc.) in the resulting signals provided by the EMG sensors (110) when the user performs a physical gesture. An initial reference gesture as described herein is used to determine the "orientation" of the EMG sensor signals. If the rotational orientation of device 100 is varied by, for example, 180 degrees, then the corresponding EMG sensor signals may also be "rotationally reoriented" by 180 degrees. If the front-to-back orientation of device 100 is varied, then the corresponding EMG sensor signals may be "front-to-back reoriented." In either case (or in both cases), the decision tree, classifier, and/or series of evaluations may be recalibrated to reflect the position and/or orientation of device 100 on the user's forearm based on the reference gesture.

The position and/or orientation of the wearable EMG device (100) may change during use (e.g., during an extended session of continuous use, such as continuous use for on the order of hours). Accordingly, the various embodiments described herein may include monitoring a quality of match between the signal data provided by the EMG sensors (110) and the gesture identified based on that signal data. In such implementations, the wearable EMG device (100) may include a non-transitory processor-readable storage medium (140) and with processor-executable instructions and/or data that, when executed by the processor (130) of the wearable EMG device (100), cause the processor (130) to monitor a quality of match between the signal data provided by the EMG sensors (110) and the gesture identified based on that signal data. If the quality of match shows signs of degradation (or, for example, the wearable EMG device (100) is unable to recognize a gesture performed by the user after one or more attempts) then the wearable EMG device (100) may be configured to prompt the user to perform or repeat the reference gesture. The wearable EMG device (100) may prompt the user to perform or repeat the reference gesture by, for example, illuminating or flashing a corresponding light emitting diode (LED) or other visual indicator, by activating a vibratory motor or other actuator providing haptic or tactile feedback to the user, and so on. Alternatively, the user may identify degradation in the accuracy of gesture identification and volunteer to perform or repeat the reference gesture. The user may signify an intent to perform or repeat the reference gesture by, for example, toggling a switch or button on the wearable EMG device (100), or by performing an unambiguously identifiable gesture such as tapping/smacking the wearable EMG device (100) multiple times in quick succession (which is clearly detected by an inertial sensor (160)), etc. The wearable EMG device (100) may be configured to sense when it has been removed by the user (e.g., by sensing an extended period of no inertial sensor activity, or by identifying erratic signals that may be produced by the EMG sensors (110) when they are no longer capacitively coupled to the user's body) and to expect a reference gesture when it is put back on by a user.

Various embodiments of the present systems, articles, and methods are described as potentially (e.g., optionally) employing at least one activation threshold. As an example, acts 201 and 202 (and in some implementations act 203) of method 200 may be repeatedly or continuously performed by the wearable EMG device (100) whenever the wearable EMG device (100) is powered on (and worn by a user). However, acts 204, 205, and 206 may only be triggered/completed when at least one signal in the set of signals provided at act 202 and/or at least one feature in the set of features determined at act 203 exceeds a threshold. In the exemplary case of the set of features comprising a set of RMS values, an RMS baseline value of each signal channel in its "rest" or "quiescent" state (i.e., when there is no muscle activity detected) may first be determined and then acts 204, 205, and 206 may only be triggered/completed when at least one RMS value in the set of RMS values determined at 203 exceeds the corresponding "rest" or "quiescent" state for that signal channel by a defined percentage, such as by 50%, by 100%, by 150%, etc. In this case, the activation threshold is represented as the percentage (%) above the "rest" or "quiescent" state that an RMS value must reach in order to trigger completion of acts 204, 205, and 206. However, a "rest" or "quiescent" state RMS value may be zero, so a person of skill in the art will appreciate that other threshold schemes may be preferred, including but not limited to: a defined percentage (%) of the mean RMS value for the signal channel, a defined percentage (%) of the maximum RMS value for the signal channel, a fixed minimum RMS value, and so on. In some implementations, the definition of the activation threshold may adjust to accommodate new data (e.g., the mean RMS value for each signal channel may be continuously, repeatedly or periodically monitored and updated when applying an activation threshold based on the mean RMS value for each signal channel). In order to limit the number of "false positives" (i.e., the number of instances where acts 204, 205, and 206 are triggered/completed when the user has not performed a deliberate gesture), it may be advantageous to implement multiple activation thresholds that must be exceeded substantially simultaneously (and/or a single activation threshold that must be exceeded by multiple values substantially simultaneously) in order to trigger completion of acts 204, 205, and 206. For example, in some implementations, acts 204, 205, and 206 of method 200 may only be triggered when multiple (e.g., at least two, or at least three, etc.) features in the set of features determined at act 203 exceed at least one activation threshold at substantially the same time (e.g., corresponding to the same time-synchronized portion or window).

In accordance with the present systems, articles, and methods, a user's reference gesture may be used to establish at least one activation threshold and/or to normalize EMG signals for that particular user. The reference gesture may be, for example, deliberately selected to involve a Maximum Voluntary Contraction, or MVC, of the user (the exemplary reference gesture described herein is an example of this, where the outward extension of the fingers and bending back of the wrist reaches a maximum point of mobility for most users) and/or the user may be, for example, instructed to perform the reference gesture with particular vigor. In either case, the reference gesture may provide reference values (for example, maximum RMS values) that may be used by the processor (130) to set activation thresholds and/or to normalize signals provided by the EMG sensors (110) for the specific user.

As described previously, a decision tree (or more generally, a classifier or series of evaluations) may be calibrated based on a reference gesture performed by a user. For example, which feature is evaluated at each decision node (301) and what value the feature is compared to when evaluated may both be calibrated based on a reference gesture performed by the user. As an alternative to, or in combination with, this approach, a wearable EMG device (100) may store, contain, or otherwise have access to multiple versions of a decision tree or classifier (e.g., a "decision tree library"), with each version being specifically well-suited for a particular user type and/or for a particular orientation of the wearable EMG device (100). For example, a wearable EMG device (100) may store, contain, or otherwise have access to a first decision tree (e.g., a decision tree library including a first decision tree) for analyzing EMG signal data for a first user type (e.g., a user with relatively skinny, hairy arms), a second decision tree (e.g., the decision tree library including a second decision tree) for analyzing EMG signal data for a second user type (e.g., a user with particularly strong EMG signals), and so on for any number of decision trees and user types. When the user performs the reference gesture (or, in some implementations, multiple iterations of the reference gesture and/or multiple reference gestures), the corresponding EMG signal data may be compared to stored templates for the reference gesture(s) corresponding to multiple different user types, and the user type that best approximates the particular user may be identified. Once the user type that best approximates the user is identified, a decision tree that is specifically designed to analyze data for that user type may be selected and implemented by the processor (130) of the wearable EMG device in performing, for example, act 204 of method 200, act 505 of method 500, and/or act 606 of method 600. Thus, throughout this specification and the appended claims, the terms "calibrating" and/or "recalibrating" in the context of a decision tree (as in, e.g., calibrating and/or recalibrating a decision tree) are used to generally refer to both of the above approaches; namely, i) setting the parameters of a fixed decision tree structure based on a determined user type and/or orientation of the wearable EMG device (100), and ii) selecting one from a set of decision trees based on a determined user type and/or orientation of the wearable EMG device (100).

The duration of a user-performed gesture may be broken down into multiple stages, such as a beginning stage, a set of middle stages, and an end stage. In accordance with the present systems, articles, and methods, a wearable EMG device (100) may store and implement multiple (i.e., two or more) decision trees in a single gesture identification process, where each decision tree is designed or otherwise suited to correspond to a respective gesture stage. For example, a first decision tree may be designed or otherwise suited to identify a user-performed gesture based on one or more feature(s) of the beginning stage of a user-performed gesture, a second decision tree may be designed or otherwise suited to identify a user-performed gesture based on one or more feature(s) of a first middle stage of a user-performed gesture, a third decision tree may be designed or otherwise suited to identify a user-performed gesture based on one or more feature(s) of a second middle stage of a user-performed gesture, and so on. The various embodiments described herein may include or be adapted to include combining the outcomes of multiple decision tree analyses where each decision tree analysis uses a respective decision tree that is designed or otherwise suited to correspond to a respective stage of a user-performed gesture. For example, in each respective iteration of acts 604-609 of method 600, acts 606 and 607 may themselves be performed multiple times, either sequentially or in parallel, with each instance employing a different decision tree. Acts 608 and 609 may then be performed using the results from the different decision tree analyses to produce a cumulative probability score that reflects analyses using multiple different decision trees.

More specifically, in a first iteration of acts 604-609 of method 600 corresponding to a first time window, acts 606 and 607 may be performed using a first decision tree that is designed or otherwise suited to correspond to the beginning stage of a user-performed gesture. In a second iteration of acts 604-609 corresponding to a second time window, acts 606 and 607 may be performed on the second time window using the first decision tree and acts 606 and 607 may be performed on the first time window using a second decision tree that is designed or otherwise suited to correspond to a first middle stage of a user-performed gesture. In a third iteration of acts 604-609 corresponding to a third time window, acts 606 and 607 may be performed on the third time window using the first decision tree, acts 606 and 607 may be performed on the second time window using the second decision tree, and acts 606 and 607 may be performed on the first time window using a third decision tree that is designed or otherwise suited to correspond to a second middle stage of a user-performed gesture. This process may continue for any number of time windows and/or any number of decision trees, with the resulting probability scores being combined or otherwise statistically analyzed to determine a largest (cumulative) probability and the corresponding gesture being identified as the user-performed gesture.

The various embodiments described herein may be implemented as an alternative to, or in combination with, the systems, articles, and methods for gesture identification described in U.S. Provisional Patent Application Ser. No. 61/881,064 (now U.S. Non-Provisional patent application Ser. No. 14/494,274), which is incorporated by reference herein in its entirety.

The various embodiments described herein provide systems, articles, and methods for enhancing the automatic gesture recognition performance of a wearable electronic device. A wearable EMG device that detects and process EMG signals is frequently described herein for illustrative purposes, but other forms of controllers (i.e., controllers that are not wearable and/or controllers that do not employ EMG sensors) may similarly be configured to implement the teachings herein. For example, instead of or in addition to employing EMG sensors and/or accelerometers providing gesture control, a controller that operates in accordance with the present systems, articles, and methods may employ, for example, tactile sensors (e.g., buttons, switches, touchpads, or keys) providing manual control, acoustic sensors providing voice-control, optical/photonic sensors providing gesture control, or any other type(s) of user-activated sensors providing any other type(s) of user-activated control. Thus, the teachings of the present systems, articles, and methods may be applied using virtually any type of controller employing sensors (including gesture-based control devices that do not make use of electromyography or EMG sensors, such as devices employing mechanomyography (MMG) sensors or other types of sensors), with the acts described herein as being performed by "at least one EMG sensor" and/or "at least one accelerometer" being more generally performed by "at least one sensor."

Throughout this specification and the appended claims, infinitive verb forms are often used. Examples include, without limitation: "to detect," "to provide," "to transmit," "to communicate," "to process," "to route," and the like. Unless the specific context requires otherwise, such infinitive verb forms are used in an open, inclusive sense, that is as "to, at least, detect," to, at least, provide," "to, at least, transmit," and so on.

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other portable and/or wearable electronic devices, not necessarily the exemplary wearable electronic devices generally described above.

For instance, the foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs). However, those skilled in the art will recognize that the embodiments disclosed herein, in whole or in part, can be equivalently implemented in standard integrated circuits, as one or more computer programs executed by one or more computers (e.g., as one or more programs running on one or more computer systems), as one or more programs executed by on one or more controllers (e.g., microcontrollers) as one or more programs executed by one or more processors (e.g., microprocessors, central processing units, graphical processing units), as firmware, or as virtually any combination thereof, and that designing the circuitry and/or writing the code for the software and or firmware would be well within the skill of one of ordinary skill in the art in light of the teachings of this disclosure.

When logic is implemented as software and stored in memory, logic or information can be stored on any processor-readable medium for use by or in connection with any processor-related system or method. In the context of this disclosure, a memory is a processor-readable medium that is an electronic, magnetic, optical, or other physical device or means that contains or stores a computer and/or processor program. Logic and/or the information can be embodied in any processor-readable medium for use by or in connection with an instruction execution system, apparatus, or device, such as a computer-based system, processor-containing system, or other system that can fetch the instructions from the instruction execution system, apparatus, or device and execute the instructions associated with logic and/or information.

In the context of this specification, a "non-transitory processor-readable medium" can be any element that can store the program associated with logic and/or information for use by or in connection with the instruction execution system, apparatus, and/or device. The processor-readable medium can be, for example, but is not limited to, an electronic, magnetic, optical, electromagnetic, infrared, or semiconductor system, apparatus or device. More specific examples (a non-exhaustive list) of the computer readable medium would include the following: a portable computer diskette (magnetic, compact flash card, secure digital, or the like), a random access memory (RAM), a read-only memory (ROM), an erasable programmable read-only memory (EPROM, EEPROM, or Flash memory), a portable compact disc read-only memory (CDROM), digital tape, and other non-transitory media.

The various embodiments described above can be combined to provide further embodiments. To the extent that they are not inconsistent with the specific teachings and definitions herein, all of the U.S. patents, U.S. patent application publications, U.S. patent applications, foreign patents, foreign patent applications and non-patent publications referred to in this specification and/or listed in the Application Data Sheet, including but not limited to U.S. Provisional Patent Application Ser. No. 61/894,263; U.S. Provisional Patent Application Ser. No. 61/857,105 (now U.S. Non-Provisional patent application Ser. No. 14/335,668); U.S. Provisional Patent Application Ser. No. 61/752,226 (now U.S. Non-Provisional patent application Ser. No. 14/155,107); U.S. Provisional Patent Application Ser. No. 61/768,322 (now U.S. Non-Provisional patent application Ser. No. 14/186,889); U.S. Provisional Patent Application Ser. No. 61/771,500 (now U.S. Non-Provisional patent application Ser. No. 14/194,252); U.S. Provisional Application Ser. No. 61/860,063 (now U.S. Non-Provisional patent application Ser. No. 14/276,575); U.S. Provisional Application Ser. No. 61/866,960 (now U.S. Non-Provisional patent application Ser. No. 14/461,044); U.S. Provisional Patent Application Ser. No. 61/869,526 (now U.S. Non-Provisional patent application Ser. No. 14/465,194); U.S. Provisional Patent Application Ser. No. 61/872,569 (now U.S. Non-Provisional patent application Ser. No. 14/471,982); and U.S. Provisional Patent Application Ser. No. 61/881,064 (now U.S. Non-Provisional patent application Ser. No. 14/494,274), are incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of operating a wearable electromyography ("EMG") device, wherein the wearable EMG device includes a set of EMG sensors and a processor communicatively coupled to the set of EMG sensors, the method comprising:

detecting muscle activity of a user of the wearable EMG device by the set of EMG sensors, wherein the muscle activity corresponds to a user-performed gesture;

in response to detecting muscle activity of the user by the set of EMG sensors, providing a set of signals from the set of EMG sensors to the processor;

determining a set of features of the set of signals by the processor;

performing a series of evaluations of at least some of the features in the set of features by the processor, wherein each evaluation in the series of evaluations includes evaluating a respective feature in the set of features by the processor, and wherein a first evaluation in the series of evaluations includes evaluating a first feature in the set of features by the processor and each subsequent evaluation in the series of evaluations is based at least in part on an outcome of a previous evaluation in the series of evaluations;

determining a respective probability score of each gesture in a gesture library by the processor based at least in part on an outcome of the series of evaluations; and identifying the user-performed gesture by the processor based at least in part on the probability score of at least one gesture in the gesture library.

2. The method of claim 1 wherein performing a series of evaluations of at least some of the features in the set of features by the processor includes performing a decision tree analysis of the set of features by the processor.

3. The method of claim 1 wherein each evaluation in the series of evaluations includes comparing a magnitude of a respective feature in the set of features to a respective value by the processor.

4. The method of claim 1 wherein determining a set of features of the set of signals by the processor includes determining at least one feature selected from the group consisting of: an average value of a signal in the set of signals, a mean value of a signal in the set of signals, a median value of a signal in the set of signals, a mode value of a signal in the set of signals, a maximum value of a signal in the set of signals, a minimum value of a signal in the set of signals, a standard deviation of a signal in the set of signals, and/or a root mean squared ("RMS") value of a signal in the set of signals.

5. The method of claim 1 wherein identifying the user-performed gesture by the processor based at least in part on the probability score of at least one gesture in the gesture library includes identifying, by the processor, a gesture in the gesture library that has a largest probability score.

6. The method of claim 1 wherein the wearable EMG device further includes a non-transitory processor-readable storage medium communicatively coupled to the processor, and wherein the non-transitory processor-readable storage medium stores processor-executable gesture identification instructions, and wherein:

determining a set of features of the set of signals by the processor includes executing, by the processor, the processor-executable gesture identification instructions to cause the processor to determine a set of features of the set of signals;

performing a series of evaluations of at least some of the features in the set of features by the processor includes executing, by the processor, the processor-executable gesture identification instructions to cause the processor to perform a series of evaluations of at least some of the features in the set of features;

determining a respective probability score of each gesture in a gesture library by the processor based at least in part on an outcome of the series of evaluations includes executing, by the processor, the processor-executable gesture identification instructions to cause the processor to determine a respective probability score of each gesture in a gesture library based at least in part on an outcome of the series of evaluations; and identifying the user-performed gesture by the processor based at least in part on the probability score of at least one gesture in the gesture library includes executing, by the processor, the processor-executable gesture identification instructions to cause the processor to identify the user-performed gesture based at least in part on the probability score of at least one gesture in the gesture library.

7. The method of claim 1 wherein the wearable EMG device further includes at least one inertial sensor, and wherein the method further comprises:

detecting motion of the wearable EMG device by the at least one inertial sensor, wherein the motion corresponds to the user-performed gesture;

in response to detecting motion of the wearable EMG device by the at least one inertial sensor, providing at least one signal from the at least one inertial sensor to the processor; and processing the at least one signal from the at least one inertial sensor by the processor, and wherein identifying the user-performed gesture by the processor based at least in part on the probability score of at least one gesture in the gesture library includes identifying the user-performed gesture by the processor based at least in part on an outcome of the processing the at least one signal from the at least one inertial sensor by the processor.

8. The method of claim 1, further comprising:

capturing a respective time-synchronized first portion of each signal in the set of signals by the processor, and wherein:

determining a set of features of the set of signals by the processor includes determining a set of features of the time-synchronized first portions of the signals in the set of signals by the processor;

performing a series of evaluations of at least some of the features in the set of features by the processor includes performing a series of evaluations of at least some of the features of the time-synchronized first portions of the signals in the set of signals by the processor; and determining a respective probability score of each gesture in a gesture library by the processor based at least in part on an outcome of the series of evaluations includes determining a respective first probability score of each gesture in the gesture library by the processor based at least in part on an outcome of the series of evaluations of at least some of the features of the time-synchronized first portions of the signals in the set of signals.

9. The method of claim 8, further comprising:

capturing a respective time-synchronized second portion of each signal in the set of signals by the processor, wherein:

determining a set of features of the set of signals by the processor includes determining a set of features of the time-synchronized second portions of the signals in the set of signals by the processor;

performing a series of evaluations of at least some of the features in the set of features by the processor includes performing a series of evaluations of at least some of the features of the time-synchronized second portions of the signals in the set of signals by the processor; and determining a respective probability score of each gesture in a gesture library by the processor based at least in part on an outcome of the series of evaluations includes determining a respective second probability score of each gesture in the gesture library by the processor based at least in part on an outcome of the series of evaluations of at least some of the features of the time-synchronized second portions of the signals in the set of signals; and generating a respective cumulative probability score of each gesture in the gesture library by the processor, wherein the respective cumulative probability score of each gesture in the gesture library combines the first probability score of the gesture and the second probability score of the gesture, and wherein identifying the user-performed gesture by the processor based at least in part on the probability score of at least one gesture in the gesture library includes identifying the user-performed gesture by the processor based at least in part on the cumulative probability score of at least one gesture in the gesture library.

10. The method of claim 1, further comprising:
in response to the user performing a reference gesture:
determining an orientation of the wearable EMG device on the user by the wearable EMG device; and
calibrating the series of evaluations by the wearable EMG device.

11. The method of claim 1 wherein:
providing a set of signals from the set of EMG sensors to the processor includes providing a respective signal from each respective EMG sensor in the set of EMG sensors to the processor; and
determining a set of features of the set of signals by the processor includes determining at least one respective feature of the signal from each respective EMG sensor in the set of EMG sensors by the processor.

12. The method of claim 1 wherein determining a respective probability score of each gesture in a gesture library by the processor based at least in part on an outcome of the series of evaluations includes determining a corresponding probability vector from a set of probability vectors by the processor based at least in part on the outcome of the series of evaluations.

13. A wearable electromyography ("EMG") device comprising:
a set of EMG sensors responsive to muscle activity corresponding to a gesture performed by a user of the wearable EMG device, wherein in response to muscle activity corresponding to a gesture performed by the user, the set of EMG sensors provide a set of signals;
a processor communicatively coupled to the set of EMG sensors; and
a non-transitory processor-readable storage medium communicatively coupled to the processor, wherein the non-transitory processor-readable storage medium stores processor-executable gesture identification instructions that, when executed by the processor, cause the processor to:
determine a set of features of the set of signals;
perform a series of evaluations of at least some of the features in the set of features by the processor, wherein each evaluation in the series of evaluations includes evaluating a respective feature in the set of features, and wherein a first evaluation in the series of evaluations includes evaluating a first feature in the set of features and each subsequent evaluation in the series of evaluations is based at least in part on an outcome of a previous evaluation in the series of evaluations;
determine a respective probability score of each gesture in a gesture library based at least in part on the series of evaluations; and
identify the gesture performed by the user based at least in part on the probability score of at least one gesture in the gesture library.

14. The wearable EMG device of claim 13, further comprising:
at least one communication terminal communicatively coupled to the processor, the at least one communication terminal to transmit information about the gesture performed by the user.

15. The wearable EMG device of claim 13, further comprising:
at least one inertial sensor communicatively coupled to the processor, the at least one inertial sensor responsive to motion corresponding to the gesture performed by the user of the wearable EMG device, wherein in response to motion corresponding to the gesture performed by the user, the at least one inertial sensor provides at least one signal, and wherein the processor-executable gesture identification instructions that, when executed by the processor, cause the processor to identify the gesture performed by the user based at least in part on the probability score of at least one gesture in the gesture library cause the processor to identify the gesture performed by the user based at least in part on both the probability score of at least one gesture in the gesture library and the at least one signal provided by the at least one inertial sensor in response to the motion.

16. The wearable EMG device of claim 13, further comprising:
a set of pod structures that form physically coupled links of the wearable EMG device, wherein each pod structure in the set of pod structures is positioned adjacent and in between two other pod structures in the set of pod structures and physically coupled to the two other pod structures in the set of pod structures, and wherein the set of pod structures forms a perimeter of an annular configuration.

17. A method of identifying which gesture in a gesture library is performed by a user of a wearable electromyography ("EMG") device, wherein the wearable EMG device includes a set of EMG sensors and a processor communicatively coupled to the set of EMG sensors, the method comprising:
in response to the user performing a gesture while wearing the wearable EMG device, detecting muscle activity of the user by the set of EMG sensors;
in response to detecting muscle activity of the user by the set of EMG sensors, providing a set of signals from the set of EMG sensors to the processor, wherein each signal in the set of signals is provided by a respective one of the EMG sensors in the set of EMG sensors;
until a cumulative probability score that exceeds a threshold value is identified, iteratively:
capturing a respective time-synchronized portion of each signal in the set of signals by the processor;
determining a set of features of the time-synchronized portions of the signals in the set of signals by the processor;
performing a decision tree analysis of the set of features by the processor;
determining a respective probability score of each gesture in the gesture library by the processor;

generating a respective cumulative probability score of each gesture in the gesture library by the processor; and comparing the cumulative probability scores in the set of cumulative probability scores to the threshold value by the processor; and in response to identifying a cumulative probability score that exceeds a threshold value:

stopping the iteration; and returning a gesture in the gesture library that corresponds to the cumulative probability score that exceeds the threshold value by the processor.

18. The method of claim 17 wherein determining a set of features of the time-synchronized portions of the signals in the set of signals by the processor includes determining at least one respective feature of the time-synchronized portion of each respective signal in the set of signals by the processor.

19. The method of claim 17 wherein performing a decision tree analysis of the set of features by the processor includes performing a series of evaluations of at least some of the features in the set of features by the processor, wherein each evaluation in the series of evaluations includes evaluating a respective feature in the set of features by the processor, and wherein a first evaluation in the series of evaluations includes evaluating a first feature in the set of features by the processor and each subsequent evaluation in the series of evaluations is based at least in part on an outcome of a previous evaluation in the series of evaluations.

20. The method of claim 17 wherein the wearable EMG device further includes at least one inertial sensor communicatively coupled to the processor, and wherein the method further comprises:

in response to the user performing the gesture while wearing the wearable EMG device, detecting motion of the wearable EMG device by the at least one inertial sensor;

in response to detecting motion of the wearable EMG device by the at least one inertial sensor, providing at least one signal from the at least one inertial sensor to the processor;

processing the at least one signal from the at least one inertial sensor by the processor; and identifying which gesture from the gesture library is performed by the user based at least in part on both the gesture in the gesture library that corresponds to the cumulative probability score that exceeds the threshold value and the processing the at least one signal from the at least one inertial sensor.

21. The method of claim 17 wherein generating a respective cumulative probability score of each gesture in the gesture library by the processor includes, for each gesture in the gesture library, combining the respective probability scores from multiple iterations.

22. The method of claim 21 wherein generating a respective cumulative probability score of each gesture in the gesture library in an $i^{th}$ iteration includes, for each gesture in the gesture library, combining the respective probability score determined in the $i^{th}$ iteration with the respective probability score determined in an $(i-1)^{th}$ iteration.

23. The method of claim 17 wherein determining a respective probability score of each gesture in the gesture library by the processor includes determining a corresponding probability vector from a set of probability vectors by the processor based at least in part on an outcome of the decision tree analysis.

24. A wearable electromyography ("EMG") device comprising:

a set of EMG sensors responsive to muscle activity corresponding to a gesture performed by a user of the wearable EMG device, wherein in response to muscle activity corresponding to a gesture performed by the user, the set of EMG sensors provide a set of signals;

a processor communicatively coupled to the set of EMG sensors; and a non-transitory processor-readable storage medium communicatively coupled to the processor, wherein the non-transitory processor-readable storage medium stores processor-executable gesture identification instructions that, when executed by the processor, cause the processor to:

i) until a cumulative probability score that exceeds a threshold value is identified, iteratively:

capture a respective time-synchronized portion of each signal in the set of signals;

determine a set of features of the time-synchronized portions of the signals in the set of signals;

perform a decision tree analysis of the set of features;

determine a respective probability score of each gesture in the gesture library;

generate a respective cumulative probability score of each gesture in the gesture library; and compare the cumulative probability scores in the set of cumulative probability scores to the threshold value; and ii) in response to identifying a cumulative probability score that exceeds a threshold value:

stop the iteration; and return the gesture in the gesture library that corresponds to the cumulative probability score that exceeds the threshold value.

25. The wearable EMG device of claim 24, further comprising:

at least one communication terminal communicatively coupled to the processor, the at least one communication terminal to transmit information about the gesture performed by the user.

26. The wearable EMG device of claim 24, further comprising:

at least one inertial sensor communicatively coupled to the processor, the at least one inertial sensor responsive to motion corresponding to the gesture performed by the user of the wearable EMG device, wherein in response to motion corresponding to the gesture performed by the user, the at least one inertial sensor provides at least one signal, and wherein the processor-executable gesture identification instructions, when executed by the processor, cause the processor to identify the gesture performed by the user based at least in part on the at least one signal provided by the at least one inertial sensor in response to the motion.

27. The wearable EMG device of claim 24, further comprising:

a set of pod structures that form physically coupled links of the wearable EMG device, wherein each pod structure in the set of pod structures is positioned adjacent and in between two other pod structures in the set of pod structures and physically coupled to the two other pod structures in the set of pod structures, and wherein the set of pod structures forms a perimeter of an annular configuration.

* * * * *